(12) United States Patent
Marotta et al.

(10) Patent No.: US 9,468,479 B2
(45) Date of Patent: Oct. 18, 2016

(54) BONE PLATE

(71) Applicant: Cardinal Health 247, Inc., Dublin, OH (US)

(72) Inventors: John Marotta, Denver, CO (US); Victoria Trafka, Colorado Springs, CO (US)

(73) Assignee: Cardinal Health 247, Inc., Dublin, OH (US)

( * ) Notice: Subject to any disclaimer, the term of this patent is extended or adjusted under 35 U.S.C. 154(b) by 270 days.

(21) Appl. No.: 14/019,827

(22) Filed: Sep. 6, 2013

(65) Prior Publication Data
US 2015/0073486 A1    Mar. 12, 2015

(51) Int. Cl.
    *A61B 17/88*     (2006.01)
    *A61B 17/80*     (2006.01)
    *A61B 17/86*     (2006.01)

(52) U.S. Cl.
    CPC ....... *A61B 17/8014* (2013.01); *A61B 17/8057* (2013.01); *A61B 17/8085* (2013.01); *A61B 17/8605* (2013.01)

(58) Field of Classification Search
None
See application file for complete search history.

(56) References Cited

U.S. PATENT DOCUMENTS

| | | |
|---|---|---|
| 3,386,437 A | 6/1968 | Treace |
| 4,530,114 A | 7/1985 | Tepic |
| 4,790,302 A | 12/1988 | Colwill |
| 5,013,313 A | 5/1991 | Surer |
| 5,041,114 A | 8/1991 | Chapman et al. |
| 5,053,036 A | 10/1991 | Perren et al. |
| 5,108,397 A | 4/1992 | White |
| 5,129,899 A | 7/1992 | Small |
| 5,151,103 A | 9/1992 | Tepic et al. |
| 5,190,544 A | 3/1993 | Chapman et al. |
| 5,318,567 A | 6/1994 | Vichard |
| 5,364,398 A | 11/1994 | Chapman |
| 5,429,641 A | 7/1995 | Gotfried |
| 5,514,138 A | 5/1996 | McCarthy |
| 5,545,228 A | 8/1996 | Kambin |
| 5,569,247 A | 10/1996 | Morrison |
| 5,578,034 A | 11/1996 | Estes |
| 5,667,506 A | 9/1997 | Sutterlin |

(Continued)

OTHER PUBLICATIONS

GMReis website, "PBA-S T of 3.5 mm", located online on Sep. 9, 2013 at: http://www.gmreis.com.br/produtos/traumatologia/micro_e_pequenos_fragmentos/pbas_t_de_35_mm, 2 pages.

(Continued)

*Primary Examiner* — Sameh Boles
(74) *Attorney, Agent, or Firm* — Adnan H. Bohri

(57) ABSTRACT

Bones fracture in any number of various ways and, in order to properly reduce a fracture, it may be necessary to place compression screws in any number of combinations along a bone plate to bring the various bone fragments together. A bone plate is provided with an optimal number and combination of threaded holes and non-threaded holes. In embodiments, the bone plate comprises one or more "hole pairs" in which a non-threaded hole and a threaded hole are placed adjacent to one another. The use of hole pairs enables a surgeon to place a compression screw and a locking screw in close proximity, facilitating both bone reduction and bone plate stabilization in a proximate location on the bone plate. In embodiments, the bone plate has an optimal thickness that promotes structural integrity while maximizing the number and combination of holes and reducing the profile of seated screws.

21 Claims, 16 Drawing Sheets

(56) References Cited

U.S. PATENT DOCUMENTS

| | | | |
|---|---|---|---|
| 5,674,222 A | 10/1997 | Berger et al. |
| 5,693,055 A | 12/1997 | Zahiri |
| 5,702,395 A | 12/1997 | Hopf |
| 5,709,686 A | 1/1998 | Talos et al. |
| 5,709,687 A | 1/1998 | Pennig |
| 5,743,912 A | 4/1998 | Lahille |
| 5,749,872 A | 5/1998 | Kyle et al. |
| 5,766,254 A | 6/1998 | Gelbard |
| 5,772,662 A | 6/1998 | Chapman et al. |
| 5,810,821 A | 9/1998 | Vandewalle |
| 5,855,580 A | 1/1999 | Kreidler |
| 5,902,303 A | 5/1999 | Eckhof |
| 5,925,048 A | 7/1999 | Ahmad et al. |
| 5,931,838 A | 8/1999 | Vito |
| 5,951,556 A | 9/1999 | Faccioli |
| 5,961,517 A | 10/1999 | Biedermann |
| 5,964,762 A | 10/1999 | Biedermann |
| 5,993,449 A | 11/1999 | Schlapfer |
| 6,007,535 A | 12/1999 | Rayhack |
| 6,007,536 A | 12/1999 | Yue |
| 6,022,352 A | 2/2000 | Vandewalle |
| 6,139,550 A | 10/2000 | Michelson |
| 6,146,382 A | 11/2000 | Hurlbert |
| 6,152,927 A | 11/2000 | Farris |
| 6,176,881 B1 | 1/2001 | Schar |
| 6,179,839 B1 | 1/2001 | Weiss et al. |
| 6,193,721 B1 | 2/2001 | Michelson |
| 6,206,882 B1 | 3/2001 | Cohen |
| 6,224,602 B1 | 5/2001 | Hayes |
| 6,228,085 B1 | 5/2001 | Theken |
| 6,235,032 B1 | 5/2001 | Link |
| 6,235,033 B1 | 5/2001 | Brace |
| 6,270,499 B1 | 8/2001 | Leu et al. |
| 6,302,883 B1 | 10/2001 | Bono |
| 6,331,179 B1 | 12/2001 | Freid |
| 6,332,780 B1 | 12/2001 | Traxel |
| 6,364,882 B1 | 4/2002 | Orbay |
| 6,383,186 B1 | 5/2002 | Michelson |
| 6,398,783 B1 | 6/2002 | Michelson |
| 6,416,528 B1 | 7/2002 | Michelson |
| 6,428,542 B1 | 8/2002 | Michelson |
| 6,432,106 B1 | 8/2002 | Fraser |
| 6,440,135 B2 | 8/2002 | Orbay et al. |
| 6,454,769 B2 | 9/2002 | Wagner |
| 6,454,770 B1 | 9/2002 | Klaue |
| 6,454,771 B1 | 9/2002 | Michelson |
| 6,506,191 B1 | 1/2003 | Joos |
| 6,527,776 B1 | 3/2003 | Michelson |
| 6,533,786 B1 | 3/2003 | Needham |
| 6,533,789 B1 | 3/2003 | Hall, IV |
| 6,585,738 B1 | 7/2003 | Mangione |
| 6,592,586 B1 | 7/2003 | Michelson |
| 6,599,290 B2 | 7/2003 | Bailey |
| 6,602,256 B1 | 8/2003 | Hayes |
| 6,613,051 B1 | 9/2003 | Luk |
| 6,613,053 B1 | 9/2003 | Collins |
| 6,616,666 B1 | 9/2003 | Michelson |
| 6,623,486 B1 | 9/2003 | Weaver et al. |
| 6,645,207 B2 | 11/2003 | Dixon |
| 6,645,209 B2 | 11/2003 | Hall, IV |
| 6,648,885 B1 | 11/2003 | Friesem |
| 6,648,891 B2 | 11/2003 | Kim |
| 6,656,181 B2 | 12/2003 | Dixon |
| 6,660,007 B2 | 12/2003 | Khanna |
| 6,669,700 B1 | 12/2003 | Farris |
| 6,669,701 B2 | 12/2003 | Steiner et al. |
| 6,682,530 B2 | 1/2004 | Dixon |
| 6,689,134 B2 | 2/2004 | Ralph |
| 6,692,503 B2 | 2/2004 | Foley |
| 6,695,845 B2 | 2/2004 | Dixon |
| 6,706,046 B2 | 3/2004 | Orbay et al. |
| 6,712,818 B1 | 3/2004 | Michelson |
| 6,712,820 B2 | 3/2004 | Orbay |
| 6,719,759 B2 | 4/2004 | Wagner et al. |
| 6,730,091 B1 | 5/2004 | Pfefferle et al. |
| 6,755,831 B2 | 6/2004 | Putnam |
| 6,755,833 B1 | 6/2004 | Paul et al. |
| 6,767,351 B2 | 7/2004 | Orbay et al. |
| 6,855,147 B2 | 2/2005 | Harrington, Jr. |
| 6,872,210 B2 | 3/2005 | Hearn |
| 6,884,242 B2 | 4/2005 | LeHuec |
| 6,884,243 B2 | 4/2005 | Sellers |
| 6,902,567 B2 | 6/2005 | Del Medico |
| 6,916,320 B2 | 7/2005 | Michelson |
| 6,926,718 B1 | 8/2005 | Michelson |
| 6,936,050 B2 | 8/2005 | Michelson |
| 6,936,051 B2 | 8/2005 | Michelson |
| 6,945,972 B2 | 9/2005 | Frigg |
| 6,945,975 B2 | 9/2005 | Dalton |
| 6,955,677 B2 | 10/2005 | Dahners |
| 6,969,390 B2 | 11/2005 | Michelson |
| 6,979,334 B2 | 12/2005 | Dalton |
| 6,989,012 B2 | 1/2006 | LeHuec |
| 7,001,387 B2 | 2/2006 | Farris |
| 7,008,426 B2 | 3/2006 | Paul |
| 7,041,105 B2 | 5/2006 | Michelson |
| 7,044,952 B2 | 5/2006 | Michelson |
| 7,070,599 B2 | 7/2006 | Paul |
| 7,070,601 B2 | 7/2006 | Culbert et al. |
| 7,077,844 B2 | 7/2006 | Michelson |
| 7,090,676 B2 | 8/2006 | Huebner et al. |
| 7,094,238 B2 | 8/2006 | Morrison et al. |
| 7,097,645 B2 | 8/2006 | Michelson |
| 7,112,202 B2 | 9/2006 | Michelson |
| 7,112,222 B2 | 9/2006 | Fraser |
| 7,115,130 B2 | 10/2006 | Michelson |
| 7,118,573 B2 | 10/2006 | Michelson |
| 7,128,744 B2 | 10/2006 | Weaver et al. |
| 7,128,760 B2 | 10/2006 | Michelson |
| 7,137,984 B2 | 11/2006 | Michelson |
| 7,137,987 B2 | 11/2006 | Patterson et al. |
| 7,169,150 B2 | 1/2007 | Shipp |
| 7,175,623 B2 | 2/2007 | Thramann |
| 7,175,624 B2 | 2/2007 | Konieczynski |
| 7,179,260 B2 | 2/2007 | Gerlach et al. |
| 7,186,256 B2 | 3/2007 | Michelson |
| 7,189,237 B2 | 3/2007 | Huebner |
| 7,195,633 B2 | 3/2007 | Medoff et al. |
| 7,204,837 B2 | 4/2007 | Paul |
| 7,229,445 B2 | 6/2007 | Hayeck et al. |
| 7,250,053 B2 | 7/2007 | Orbay |
| 7,282,053 B2 | 10/2007 | Orbay |
| 7,288,095 B2 | 10/2007 | Baynham |
| 7,294,130 B2 | 11/2007 | Orbay |
| 7,316,687 B2 | 1/2008 | Aikins et al. |
| 7,318,825 B2 | 1/2008 | Butler |
| 7,326,212 B2 | 2/2008 | Huebner |
| 7,331,961 B2 | 2/2008 | Abdou |
| 7,341,589 B2 | 3/2008 | Weaver et al. |
| 7,341,590 B2 | 3/2008 | Ferree |
| 7,344,537 B1 | 3/2008 | Mueller |
| 7,354,441 B2 | 4/2008 | Frigg |
| 7,399,301 B2 | 7/2008 | Michelson |
| 7,438,715 B2 | 10/2008 | Doubler |
| 7,479,143 B2 | 1/2009 | Suh |
| 7,491,221 B2 | 2/2009 | David |
| 7,503,919 B2 | 3/2009 | Shaw |
| 7,537,596 B2 | 5/2009 | Jensen |
| 7,547,306 B2 | 6/2009 | Michelson |
| 7,578,835 B2 | 8/2009 | Wang |
| 7,588,576 B2 | 9/2009 | Teague |
| 7,604,657 B2 | 10/2009 | Orbay |
| 7,635,364 B2 | 12/2009 | Barrall et al. |
| 7,635,381 B2 | 12/2009 | Orbay |
| 7,651,497 B2 | 1/2010 | Michelson |
| 7,662,154 B2 | 2/2010 | Ribeiro |
| 7,670,341 B2 | 3/2010 | Leyden |
| 7,678,113 B2 | 3/2010 | Melkent |
| 7,686,836 B2 | 3/2010 | Johnston |
| 7,695,472 B2 | 4/2010 | Young |
| 7,704,250 B2 | 4/2010 | Michelson |
| 7,704,251 B2 | 4/2010 | Huebner et al. |
| 7,704,255 B2 | 4/2010 | Michelson |
| 7,717,945 B2 | 5/2010 | Jensen et al. |

(56) References Cited

U.S. PATENT DOCUMENTS

| | | | |
|---|---|---|---|
| 7,722,653 B2 | 5/2010 | Young et al. |
| 7,740,630 B2 | 6/2010 | Michelson |
| 7,740,648 B2 | 6/2010 | Young |
| 7,740,649 B2 | 6/2010 | Mosca |
| 7,766,911 B1 | 8/2010 | Navarro et al. |
| 7,766,947 B2 | 8/2010 | Hawkes |
| 7,771,457 B2 | 8/2010 | Kay |
| 7,776,076 B2 | 8/2010 | Grady, Jr. et al. |
| 7,780,667 B2 | 8/2010 | Watanabe et al. |
| 7,780,710 B2 | 8/2010 | Orbay |
| 7,780,711 B2 | 8/2010 | Orbay |
| 7,785,327 B1 | 8/2010 | Navarro et al. |
| 7,799,061 B2 | 9/2010 | Kay |
| 7,803,157 B2 | 9/2010 | Michelson |
| 7,811,285 B2 | 10/2010 | Michelson |
| 7,811,312 B2 | 10/2010 | Stevens |
| 7,824,432 B2 | 11/2010 | Michelson |
| 7,833,226 B2 | 11/2010 | Grabowski |
| 7,837,689 B2 | 11/2010 | Leyden |
| 7,837,717 B2 | 11/2010 | Deffenbaugh |
| 7,857,839 B2 | 12/2010 | Duong |
| 7,867,261 B2 | 1/2011 | Sixto, Jr. |
| 7,875,033 B2 | 1/2011 | Richter |
| 7,883,531 B2 | 2/2011 | de Coninck |
| 7,887,547 B2 | 2/2011 | Campbell |
| 7,887,570 B2 | 2/2011 | Ziolo et al. |
| 7,901,433 B2 | 3/2011 | Forton |
| 7,905,883 B2 | 3/2011 | Bruecker |
| 7,905,909 B2 | 3/2011 | Orbay et al. |
| 7,905,910 B2 | 3/2011 | Gerlach et al. |
| 7,909,858 B2 | 3/2011 | Gerlach |
| 7,909,859 B2 | 3/2011 | Mosca |
| 7,909,860 B2 | 3/2011 | Rathbun et al. |
| 7,918,853 B2 | 4/2011 | Watanabe |
| 7,927,341 B2 | 4/2011 | Orbay |
| 7,931,652 B2 | 4/2011 | Ferrante |
| 7,931,678 B2 | 4/2011 | Konieczynski |
| 7,938,850 B2 | 5/2011 | Orbay |
| 7,942,912 B2 | 5/2011 | Brockmeyer |
| 7,951,176 B2 | 5/2011 | Grady, Jr. |
| 7,951,178 B2 | 5/2011 | Jensen |
| 7,963,980 B1 | 6/2011 | Freeman |
| 7,976,570 B2 | 7/2011 | Wagner et al. |
| 7,981,141 B2 | 7/2011 | Morrison et al. |
| 7,985,224 B2 | 7/2011 | Michelson |
| 7,998,179 B2 | 8/2011 | Lindemann |
| 7,998,180 B2 | 8/2011 | Erickson |
| 8,002,808 B2 | 8/2011 | Morrison et al. |
| 8,021,402 B2 | 9/2011 | Martin et al. |
| 8,029,551 B2 | 10/2011 | Running et al. |
| 8,043,333 B2 | 10/2011 | Frigg |
| 8,048,075 B2 | 11/2011 | Michelson |
| 8,048,076 B2 | 11/2011 | Michelson |
| 8,057,520 B2 | 11/2011 | Ducharme |
| 8,062,296 B2 | 11/2011 | Orbay et al. |
| 8,070,784 B2 | 12/2011 | LeHuec |
| 8,080,010 B2 | 12/2011 | Schulz et al. |
| 8,100,953 B2 | 1/2012 | White |
| 8,100,954 B2 | 1/2012 | Kay |
| 8,105,367 B2 | 1/2012 | Austin |
| 8,118,846 B2 | 2/2012 | Leither |
| 8,118,848 B2 | 2/2012 | Ducharme et al. |
| 8,123,788 B2 | 2/2012 | Michelson |
| 8,142,485 B2 | 3/2012 | Buhren |
| 8,152,838 B2 | 4/2012 | Ensign |
| 8,157,803 B1 | 4/2012 | Zirkle, Jr. et al. |
| 8,162,996 B2 | 4/2012 | Schelling |
| 8,167,918 B2 | 5/2012 | Strnad |
| 8,167,919 B2 | 5/2012 | Foley |
| 8,182,485 B1 | 5/2012 | Gonzalez-Hernandez |
| 8,182,517 B2 | 5/2012 | Sixto, Jr. et al. |
| 8,182,518 B2 | 5/2012 | Butler |
| 8,192,472 B2 | 6/2012 | Sixto, Jr. |
| 8,197,521 B2 | 6/2012 | Sixto, Jr. |
| 8,221,476 B2 | 7/2012 | Paul |
| 8,231,663 B2 | 7/2012 | Kay |
| 8,236,033 B2 | 8/2012 | Paul |
| 8,241,337 B2 | 8/2012 | Brockmeyer |
| 8,246,661 B2 | 8/2012 | Beutter |
| 8,246,664 B2 | 8/2012 | Terrill |
| 8,257,403 B2 | 9/2012 | Den Hartog |
| 8,257,406 B2 | 9/2012 | Kay |
| 8,262,707 B2 | 9/2012 | Huebner |
| 8,262,708 B2 | 9/2012 | Michelson |
| 8,267,972 B1 | 9/2012 | Gehlert |
| 8,273,111 B2 | 9/2012 | Amato |
| 8,317,842 B2 | 11/2012 | Graham |
| 8,323,283 B2 | 12/2012 | Michelson |
| 8,323,320 B2 | 12/2012 | Lowry |
| 8,328,853 B2 | 12/2012 | Ibrahim et al. |
| 8,337,535 B2 | 12/2012 | White et al. |
| 8,343,154 B2 | 1/2013 | Long |
| 8,348,980 B2 | 1/2013 | Prasad |
| 8,348,981 B2 | 1/2013 | Cheema |
| 8,353,939 B2 | 1/2013 | Anderson |
| 8,361,075 B2 | 1/2013 | Gonzalez-Hernandez |
| 8,361,127 B2 | 1/2013 | Biedermann |
| 8,388,665 B2 | 3/2013 | Eberlein |
| 8,394,098 B2 | 3/2013 | Orbay |
| 8,394,130 B2 | 3/2013 | Orbay |
| 8,403,967 B2 | 3/2013 | Orbay |
| 8,414,582 B2 | 4/2013 | Overes |
| 8,425,514 B2 | 4/2013 | Anderson |
| 8,425,569 B2 | 4/2013 | O'Farrell |
| 8,439,918 B2 | 5/2013 | Gelfand |
| 8,439,955 B2 | 5/2013 | Sixto, Jr. |
| 8,444,680 B2 | 5/2013 | Dooney, Jr. |
| 8,444,681 B2 | 5/2013 | Jackson |
| 8,454,666 B2 | 6/2013 | Tornier |
| 8,475,504 B2 | 7/2013 | Gillard |
| 8,480,716 B2 | 7/2013 | Perrow |
| 8,480,717 B2 | 7/2013 | Michelson |
| 8,486,117 B2 | 7/2013 | de Coninck |
| 8,496,659 B2 | 7/2013 | Dell'oca |
| 8,496,690 B2 | 7/2013 | Sixto |
| 8,496,693 B2 | 7/2013 | Robinson |
| 8,506,567 B2 | 8/2013 | Ziemek |
| 8,512,339 B2 | 8/2013 | Medoff |
| 8,523,862 B2 | 9/2013 | Murashko, Jr. |
| 8,523,919 B2 | 9/2013 | Huebner |
| 8,529,608 B2 | 9/2013 | Terrill |
| 8,535,355 B2 | 9/2013 | Prasad |
| 8,540,726 B2 | 9/2013 | Yevmenenko |
| 8,545,539 B2 | 10/2013 | Spencer |
| 8,545,540 B2 | 10/2013 | Castaneda |
| 8,551,095 B2 | 10/2013 | Fritzinger |
| 8,551,144 B2 | 10/2013 | Youssef |
| 8,556,943 B2 | 10/2013 | Worcel |
| 8,574,234 B2 | 11/2013 | Gonzalez-Hernandez |
| 8,574,268 B2 | 11/2013 | Chan |
| 8,574,271 B2 | 11/2013 | Crainich |
| 8,574,272 B2 | 11/2013 | Wallenstein |
| 8,579,945 B2 | 11/2013 | Appenzeller |
| 8,579,946 B2 | 11/2013 | Orbay |
| 8,585,742 B2 | 11/2013 | Windolf |
| 8,603,147 B2 | 12/2013 | Sixto, Jr. |
| 8,603,148 B2 | 12/2013 | Raven, III |
| 8,623,019 B2 | 1/2014 | Perrow |
| 8,632,545 B2 | 1/2014 | Sarangapani |
| 8,632,574 B2 | 1/2014 | Kortenbach |
| 8,636,779 B2 | 1/2014 | Butler |
| 8,641,740 B2 | 2/2014 | Kuster |
| 8,641,741 B2 | 2/2014 | Murashko, Jr. |
| 8,641,743 B2 | 2/2014 | Michelson |
| 8,641,744 B2 | 2/2014 | Weaver |
| 8,652,179 B2 | 2/2014 | Graham |
| 8,652,180 B2 | 2/2014 | Federspiel |
| 8,657,820 B2 | 2/2014 | Kubiak |
| 8,668,723 B2 | 3/2014 | Altarac |
| 8,690,927 B2 | 4/2014 | Dunn |
| 8,696,715 B2 | 4/2014 | Sidebotham |

(56) References Cited

U.S. PATENT DOCUMENTS

| | | | |
|---|---|---|---|
| 8,709,054 B2 | 4/2014 | Lowry | |
| 8,734,494 B2 | 5/2014 | Simon | |
| 2006/0229619 A1* | 10/2006 | Orbay | A61B 17/80 606/71 |

OTHER PUBLICATIONS

GMReis website, "Narrow PBA-S 4.5 mm", located online on Sep. 9, 2013 at: http://www.gmreis.com.br/produtos/traumatologia/grandes_fragmentos/pbas_45_mm_estreita, 2pgs.

GMReis website, "Narrow PBA-S 4.5 mm", located online on Sep. 9, 2013 at: http://www.gmreis.com.br/produtos/traumatologia/grandes_fragmentos/pbas_45_mm_larga, 2 pgs.

GMReis website, "T PBA-S 4.5 mm", located online on Sep. 9, 2013 at: http://www.gmreis.com.br/produtos/traumatologia/grandes_fragmentos/pbas_45_mm_t, 2 pgs.

GMReis website, "PBA-S 3.5 mm", located online on Sep. 9, 2013 at: http://www.gmreis.com.br/produtos/traumatologia/micro_e_pequenos_fragmentos/pbas_35_mm, 2 pgs.

GMReis website, "Volar PBA-S", located online on Sep. 9, 2013 at: http://www.gmreis.com.br/produtos/traumatologia/radio/pbas_volar, 2 pgs.

* cited by examiner

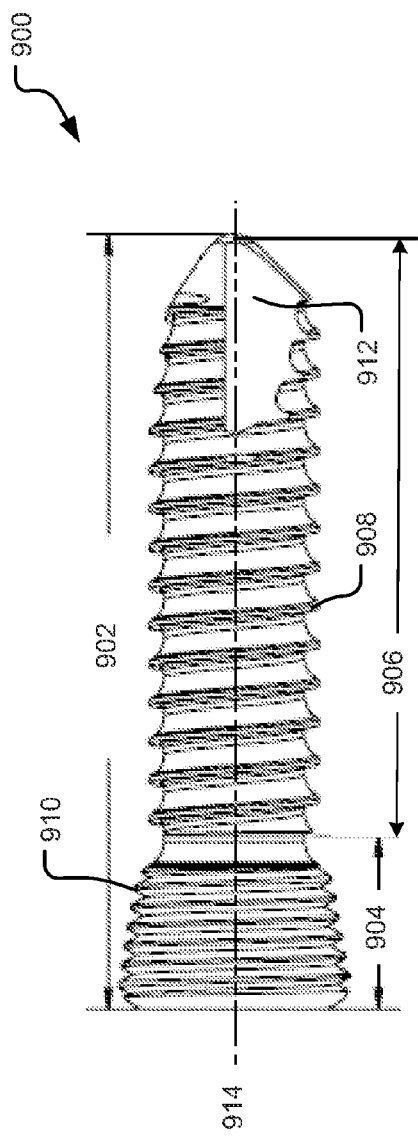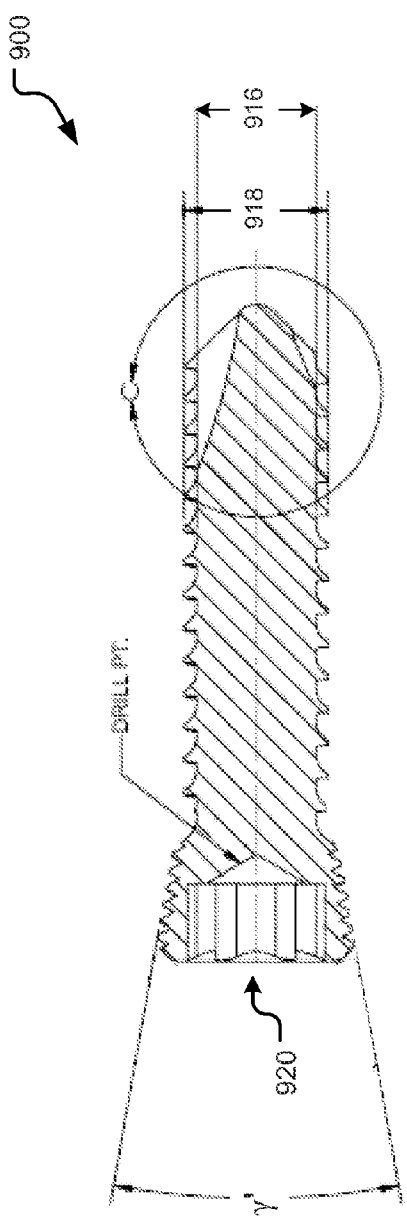

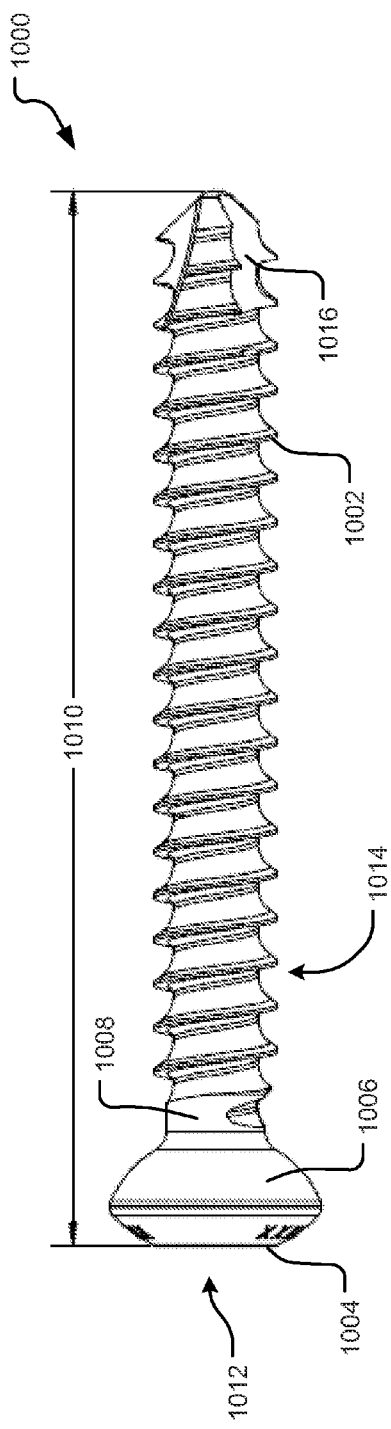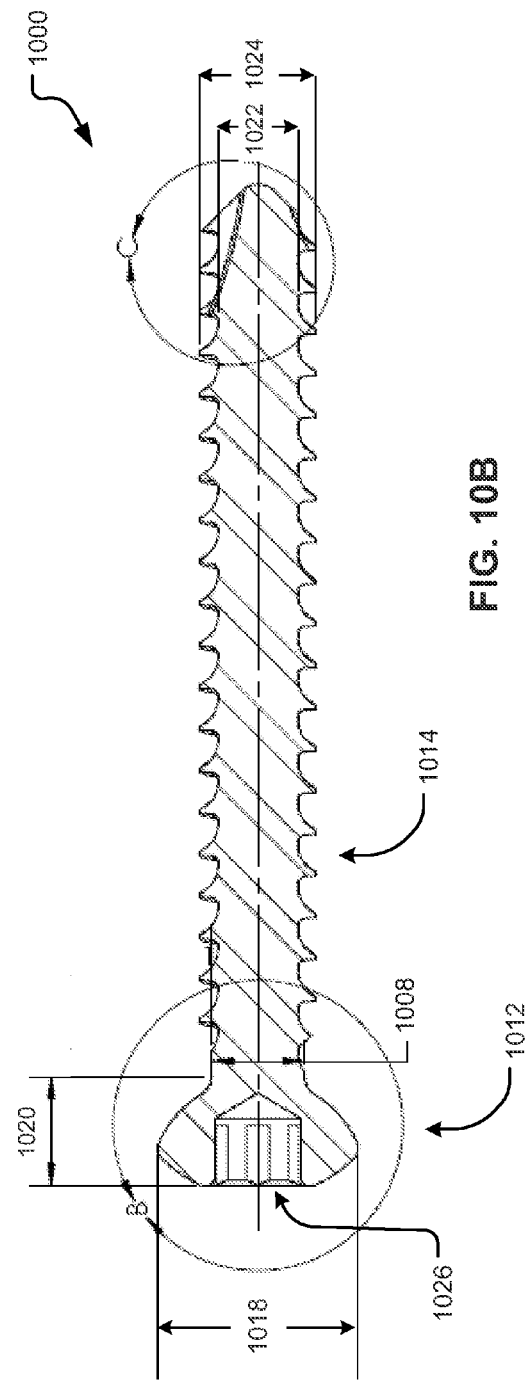
FIG. 10A
FIG. 10B

BONE PLATE

INTRODUCTION

Bone plates are used to provide structural support for fixation of various types of bone fractures. Bone plates are generally constructed of metal, e.g., titanium, and may be fabricated in a number of different shapes and sizes to conform to different types of bone for use with different types of fractures. In operation, bone plates are secured to the bone to "reduce" the fracture, i.e., bring bone fragments into alignment and close proximity to facilitate the body's natural bone growth and healing. Bone reduction is generally accomplished using compression screws. Compression screws have threaded shafts and are anchored through holes in the bone plate and into the various bone fragments, which upon tightening pull the bone fragments together under a compression load against the plate. However, due to dynamic loading caused by physiological movement, the angular relationship between the bone plate and the compression screws may loosen over time.

Securing or locking screws may be anchored both to the bone plate and to the bone to provide a fixed angular relationship between the bone plate and the locking screws, which reduces the incidence of loosening. A locking screw has a threaded head, which mates with corresponding threads of a threaded hole in the bone plate, and a threaded shaft, which anchors to the bone. Thus, as a locking screw is secured to both the bone and the bone plate, movement between the bone plate and the locking screws is reduced. As the relationship between the locking screws and the bone plate is fixed, locking screws provide a high resistance to shear or torsional forces. However, locking screws have a limited capability to compress bone fragments.

Thus, a combination of compression and locking screws may be employed with a bone plate to promote reduction of bone fractures while also preventing loosing and movement between the bone plate and the screws. Accordingly, bone plates may be configured with a combination of threaded and non-threaded holes. It is possible to insert compression screws in either threaded or non-threaded holes; however, non-threaded holes are better adapted to receive compression screws. In contrast, locking screws are only utilized with threaded holes. The limitations on the types of holes that accommodate compression screws versus locking screws has led to a number of different hole configurations for bone plates. For instance, non-threaded holes may be elongated or may be at least partially threaded to accommodate additional combinations of locking and compression screws.

It is with respect to these and other general considerations that embodiments have been made. Also, although relatively specific problems have been discussed, it should be understood that the embodiments should not be limited to solving the specific problems identified in the background.

BONE PLATE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Bones fracture in any number of various ways, including linear fractures, transverse fractures, oblique fractures, spiral fractures, comminuted fractures, etc. Accordingly, in order to properly reduce a fracture, it may be necessary to place compression screws in any number of combinations along a bone plate to bring various bone fragments together. It may also be necessary to place locking screws at various locations along the bone plate to prevent movement of the bone plate. Thus, to properly treat a variety of fractures, a bone plate is provided with an optimal number and combination of threaded holes and non-threaded holes. In embodiments, the bone plate comprises one or more "hole pairs" in which a non-threaded hole and a threaded hole are placed adjacent to one another. The use of hole pairs enables a surgeon to place a compression screw and a locking screw in close proximity, facilitating both bone reduction and bone plate stabilization in a proximate location on the bone plate. Moreover, in embodiments, the bone plate has an optimal thickness that promotes structural integrity while maximizing the number and combination of holes and reducing the profile of seated screws.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the claims.

BRIEF DESCRIPTION OF THE DRAWINGS

The following drawing figures, which form a part of this application, are illustrative of described technology and are not meant to limit the scope of the claims in any manner, which scope shall be based on the claims appended hereto.

FIGS. 9A-9B are diagrams illustrating multiple views of an embodiment of a locking screw.

FIGS. 10A-10B are diagrams illustrating multiple views of an embodiment of a compression screw.

DETAILED DESCRIPTION

Various embodiments are described more fully below with reference to the accompanying drawings, which form a part hereof, and which show specific exemplary embodiments. However, embodiments may be implemented in many different forms and should not be construed as limited to the embodiments set forth herein; rather, these embodiments are provided so that this disclosure will be thorough and complete, and will fully convey the scope of the embodiments to those skilled in the art. Embodiments may be practiced as methods, systems, or devices. The following detailed description is, therefore, not to be taken in a limiting sense.

Bones fracture in any number of various ways and, in order to properly reduce a fracture, it may be necessary to place compression screws in any number of combinations along a bone plate to bring the various bone fragments together. A bone plate is provided with an optimal number and combination of threaded holes and non-threaded holes. In embodiments, the bone plate comprises one or more "hole pairs" in which a non-threaded hole and a threaded hole are placed adjacent to one another. The use of hole pairs enables a surgeon to place a compression screw and a locking screw in close proximity, facilitating both bone reduction and bone plate stabilization in a proximate location on the bone plate. Moreover, in embodiments, the bone plate has an optimal thickness that promotes structural integrity while maximizing the number and combination of holes and reducing the profile of seated screws.

These and other embodiments will be discussed in further detail with reference to the following figures.

FIGS. 1A-1D are diagrams illustrating multiple views of an embodiment of a bone plate.

Figure 1A:
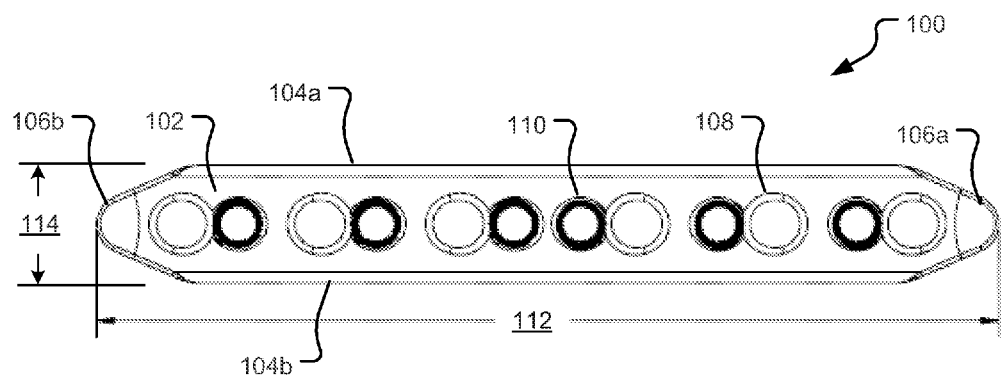
FIGS. 1A-1D are diagrams illustrating multiple views of an embodiment of a bone plate.

FIG. 1A is a top view of an embodiment of a bone plate 100.

As illustrated in FIG. 1A, bone plate 100 is substantially solid and comprises a top surface 102 and lateral surfaces 104a and 104b. Bone plate 100 may be constructed of any strong, light-weight, non-reactive material, e.g., titanium or other alloy or metal, which is suitable for implantation in a human or animal body. Although bone plate 100 is illustrated as a straight plate, bone plates may be fabricated in a number of different shapes and sizes to conform to different types of bone and for use with different types of fractures. Accordingly, disclosure that is provided herein with respect to a straight plate is also applicable to other plate geometries, e.g., bone plates having "T" or "Y" configurations.

Bone plate 100 may have a length 112 along a longitudinal axis from plate end 106a to plate end 106b. For example, length 112 may be any suitable length, e.g., from about 50 to about 400 millimeters (mm). Bone plate 100 may also have a width 114 from lateral surface 104a to lateral surface 104b. For example width 114 may be any suitable width, e.g., from about 5 to about 25 mm. In some embodiments, top surface 102 of bone plate 100 may be relatively smooth and bone plate 100 may be laterally tapered toward a longitudinal centerline at either or both plate ends 106a and 106b. Moreover, bone plate 100 may have a smooth, rounded transition from top surface 102 to lateral surfaces 104a and 104b.

Bone plate 100 further comprises one or more non-threaded holes 108 and one or more threaded holes 110. For example, non-threaded hole 108 and threaded hole 110 pass through top surface 102, through a substantially solid interior region of bone plate 100, and out bottom surface 116 (see FIG. 1C). Non-threaded hole 108 is configured to receive a compression screw (also referred to as a non-locking or reduction screw), which does not have a threaded head. The compression screw (not shown) passes through non-threaded hole 108 and into two or more bone fragments. Upon tightening the compression screw, the two or more bone fragments are pulled together under a compression load against the bottom surface 116 of bone plate 100. In contrast, threaded hole 110 comprises threads adapted to engage or mate with threads on a head of a locking screw. In embodiments, the threads of threaded hole 110 secure the locking screw to the bone plate 100 at a substantially fixed angular orientation.

In embodiments, seating of compression screws in non-threaded holes 108 reduces bone fragments against the bottom surface 116 and seating of locking screws in threaded holes 110 secures the threaded heads of the locking screws to the bone plate 100 to maintain a fixed angular relationship between the locking screws and the bone plate 100. Thus, in embodiments, use of both compression and locking screws provides stability between the locking screws and bone plate 100 and between the bone plate 100 and the underlying bone.

Figure 1B:
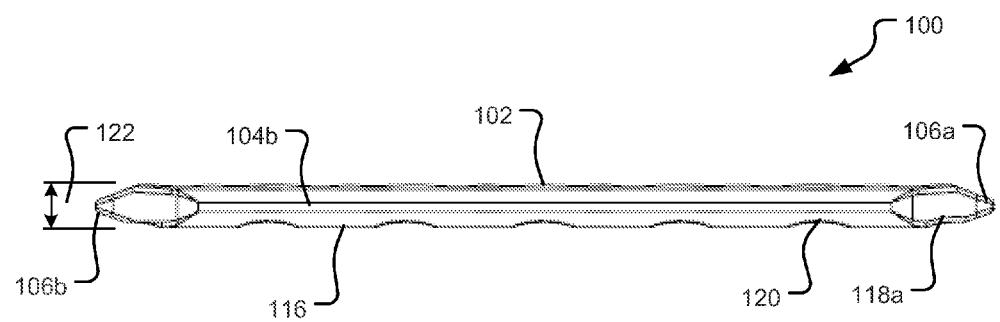

FIG. 1B is a lateral view of an embodiment of a bone plate 100.

As illustrated in FIG. 1B, bone plate 100 may have a thickness 122 between top surface 102 and bottom surface 116. For example, thickness 122 may be any suitable thickness, e.g., from about 1.5 mm to about 5.0 mm. In some embodiments, bone plate 100 may be thicker than a standard bone plate, e.g., about 0.2 mm thicker than a standard bone plate. In addition to being laterally tapered at either or both plate ends 106a and 106b, bone plate 100 is also vertically tapered toward a horizontal centerline at either or both plate ends 106a and 106b. Thus, bone plate 100 is bi-directionally tapered to form a rounded, substantially rectangular pyramid at either or both plate ends 106a and 106b. Tapering facilitates insertion of bone plate 100 under the skin in less-invasive surgical procedures. That is, in some embodiments, bone plate 100 may be inserted through a small incision and slid into place on the bone. The tapered ends 106a and 106b and the smooth, curved surfaces of bone plate 100 promote insertion of the bone plate 100. Additionally, in embodiments, smooth, curved transitions from one surface of bone plate 100 to another may reduce abrasion and irritation of surrounding tissues.

As illustrated in FIG. 1B, bone plate 100 may also comprise an indentation 118a on bottom surface 116 at either or both plate ends 106a and 106b. The indentation 118a may further facilitate insertion of bone plate 100 under the skin of a patient. Additionally, bone plate 100 may include scallops 120 on bottom surface 116. Scallops 120 may reduce contact between bone plate 100 and the bone, which increases blood flow to the bone. Scallops 120 also create a more uniform stiffness across the length of the bone plate 100, thereby reducing stresses in the bone plate that may be caused by plate contouring or may occur after plate implantation.

Figure 1C:
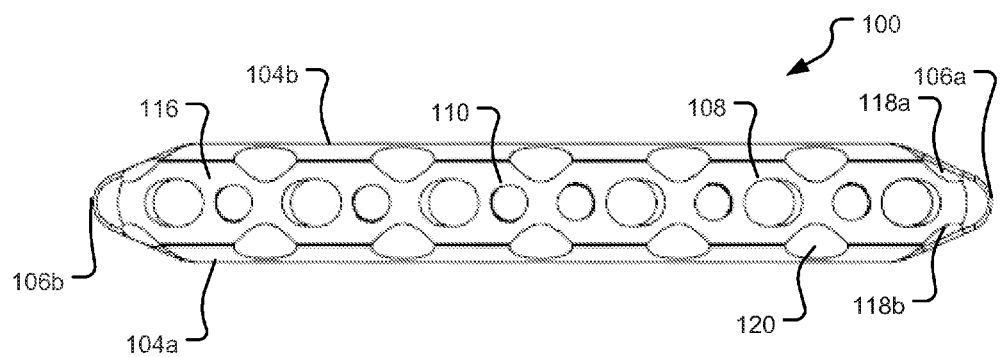

FIG. 1C is a bottom view of an embodiment of a bone plate 100.

As illustrated by FIG. 1C, bone plate 100 comprises a bottom surface 116 and lateral surfaces 104a and 104b. As with the transition from the top surface to lateral surfaces 104a and 104b, bone plate 100 may have a smooth, rounded transition from bottom surface 116 to lateral surfaces 104a and 104b. As described above, bone plate 100 further comprises one or more non-threaded holes 108 and one or more threaded holes 110, which pass through top surface 102, through a substantially solid interior region of bone plate 100, and out bottom surface 116.

As illustrated in FIG. 1C, bone plate 100 includes indentations 118a and 118b on lateral sides of plate ends 106a and 106b on bottom surface 116. The indentations 118a and 118b may further facilitate insertion of bone plate 100 under the skin of a patient. Additionally, bone plate 100 includes scallops 120 on bottom surface 116. As illustrated in FIG. 1C, scallops 120 are laterally placed between pairs of threaded and non-threaded holes on bottom surface 116.

Figure 1D:
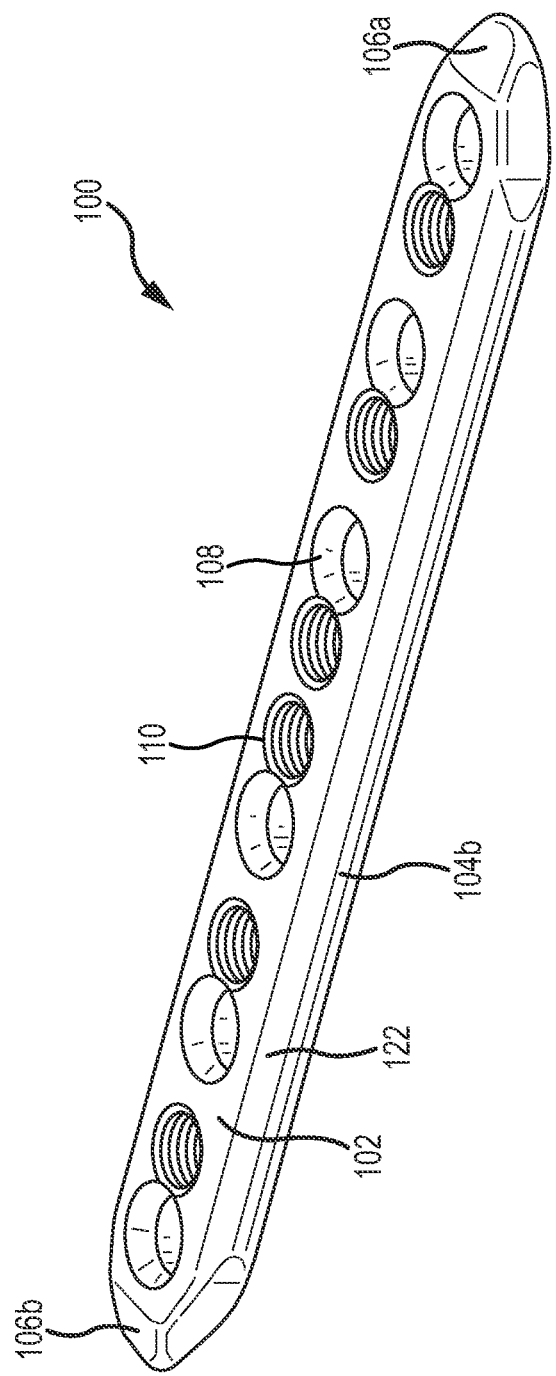

FIG. 1D is a perspective view of an embodiment of a bone plate 100.

As illustrated by FIG. 1D, bone plate 100 comprises a top surface 102 and lateral surface 104b. Moreover, the smooth, rounded transition 124 from top surface 102 to lateral surface 104b is visible in FIG. 1D. As described above, bone plate 100 further comprises one or more non-threaded holes 108 and one or more threaded holes 110. Dual tapering, both laterally and vertically, of plate ends 106a and 106b is also visible in FIG. 1D.

As should be appreciated, bone plate 100 is exemplary and explanatory and is intended to provide further explanation of the claims. However, it is contemplated that bone plate 100 may have more or fewer features within the spirit of the present disclosure and description of the various features of bone plate 100 is not intended to be limiting.

Figure 2A:
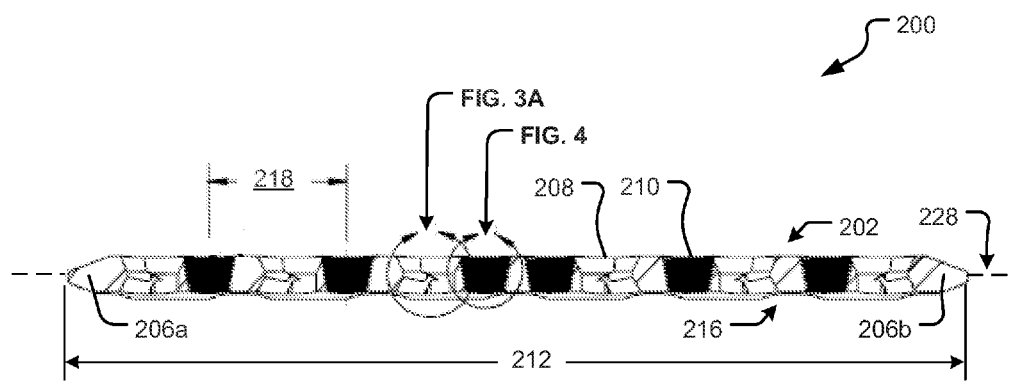
FIGS. 2A-2B are diagrams illustrating multiple views of an embodiment of a bone plate.
Figure 2B:
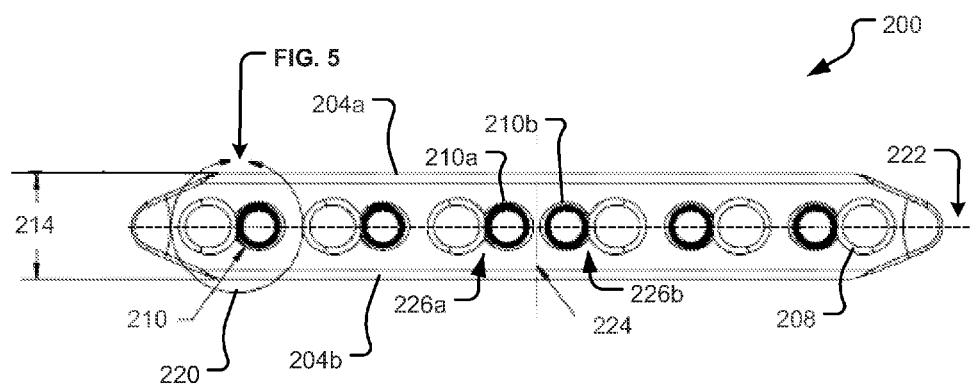

FIGS. 2A and 2B are diagrams illustrating multiple views of an embodiment of a bone plate.

FIG. 2A is a diagram illustrating a cross-sectional view of an embodiment of a bone plate 200. Bone plate 200 is substantially similar to bone plate 100.

As illustrated by FIG. 2A, bone plate 200 comprises one or more non-threaded holes 208 and one or more threaded holes 210. The cross-sectional view of bone plate 200 illustrates that non-threaded holes 208 have a first type of internal geometry and threaded holes 210 have a second type of internal geometry. For example, threaded holes 210 may be tapered from a top surface 202 through bone plate 200 to a bottom surface 216. In contrast, non-threaded holes 208 may have an upper taper extending from the top surface 202 to about a horizontal centerline 228 of the bone plate 200 and at least a partial lower taper extending from the bottom surface 216 to about the horizontal centerline 228 of the bone plate 200. The internal geometry of a non-threaded hole 208 is further described with respect to FIGS. 3A and 3B and the internal geometry of a threaded hole 210 is further described with respect to FIG. 4.

Bone plate 200 may have a length 212 along a longitudinal axis from plate end 206a to plate end 206b and a width 214 from lateral side 204a to lateral side 204b (see FIG. 2B). For example, length 212 may be any suitable length, e.g., from about 50 to about 400 mm, and width 214 may be any suitable width, e.g., from about 5 to about 25 mm. It will be appreciated that the number and combination of threaded holes 210 and non-threaded holes 208 provided on bone plate 200 is limited by the length 212, the width 214, and a thickness of bone plate 200. However, as will be appreciated, bones may fracture in any number of various ways, including linear fractures, transverse fractures, oblique fractures, spiral fractures, comminuted fractures, etc. Moreover, a combination of fractures and fracture types may occur in a single bone. Accordingly, in order to properly reduce a fracture, it may be necessary to place compression screws in any number of positions or screw orientations along a bone plate to bring the various bone fragments together. Moreover, it may be necessary to place locking screws at various locations along the bone plate to prevent movement of the bone plate. Thus, to properly treat a variety of fractures, it would be advantageous for the bone plate 200 to include an optimal number and combination of non-threaded holes 208 and threaded holes 210. In embodiments, the bone plate is provided that comprises one or more "hole pairs" in which a non-threaded hole and a threaded hole are placed adjacent to one another. The use of hole pairs enables a surgeon to concurrently place a compression screw and a locking screw in close proximity, facilitating both bone reduction and bone plate stabilization in a proximate location on the bone plate.

Prior bone plate systems were provided with "combination holes." These combination holes involved a single hole with a threaded portion and a non-threaded portion. While this prior configuration provided alternatives with regard to placing either a compression or a locking screw in each combination hole, only one type of screw could be placed in any one combination hole. Accordingly, use of combination holes limits a total number of screws that can be inserted in a bone plate. For example, for a bone plate having five (5) combination holes, while either a compression or a locking screw may be placed in each of the 5 combination holes, a maximum of 5 screws may be placed in the bone plate. Additionally, use of combination holes limits the number of screw combinations because only one type of screw may be inserted in any one combination hole. Using the above example, for a bone plate having five (5) combination holes (without taking position into consideration), possible combinations include: (a) 5-compression screws; (b) 1-locking screw, 4-compression screws; (c) 2-locking screws, 3-compression screws; (d) 3-locking screws, 2-compression screws; (e) 4-locking screws, 1-compression screw; and (f) 5-locking screws.

Conversely, for a bone plate having hole pairs, either or both of a locking screw and a compression screw may be placed in each hole pair. Thus, hole pairs maximize a total number of screws that may be inserted in a bone plate. For example, for a bone plate having five (5) hole pairs, a maximum of 10 screws may be placed in the bone plate (i.e., 5 compression screws and 5 locking screws). Moreover, hole pairs maximize the different screw combinations that may be inserted in the bone plate. As should be appreciated, when utilizing hole pairs, a locking screw, a compression screw, or both, may be placed in each hole pair. Thus, without taking position into consideration, a few of the possible combinations include: (a) 5-locking screws, no compression screws; (b) 5-locking screws, 1-compression screw; (c) 5-locking screws, 2-compression screws; (d) 5-locking screws, 3-compression screws; (e) 5-locking screws, 4-compression screws; (f) 5-locking screws, 5-compression screws; (g) 4-locking screws, no compression screws; (h) 4-locking screws, 1-compression screw; (i) 4-locking screws, 2-compression screws; (j) 4-locking screws, 3-compression screws, etc.

In embodiments, a distance 218 between center points of adjacent threaded holes 210 may be optimized to provide the greatest number of hole pairs while maintaining a sufficient structural integrity of the bone plate 200. It will be appreciated that increasing the number of holes in a bone plate having a fixed length and width (e.g., by placing holes closer together) may result in a corresponding decrease in structural integrity. Thus, in some embodiments, a thickness and scallop size of bone plate 200 may also be adjusted to optimize the structural integrity of the bone plate while at the same time maximizing the number and combination of holes in the bone plate.

FIG. 2B is a diagram illustrating a top view of an embodiment of a bone plate 200. Bone plate 200 is substantially similar to bone plate 100.

As illustrated by FIG. 2B, bone plate 200 comprises one or more non-threaded holes 208 and one or more threaded holes 210. As described above, a non-threaded hole 208 and a threaded hole 210 may be placed in close proximity to provide a "hole pair." For example, a hole pair 220 is identified by a circle and is further described with respect to FIG. 5.

A longitudinal centerline 222 is also illustrated by FIG. 2B. As described above, plate ends 206a and 206b are tapered toward longitudinal centerline 222. Bone plate 200 is further illustrated with a lateral centerline 224. In embodiments, the one or more non-threaded holes 208 and one or more threaded holes 210 may be provided so as to be substantially bisected by longitudinal centerline 222. Additionally, features of bone plate 200 may be mirrored at lateral centerline 224. For example, in one embodiment, each hole pair may be arranged such that non-threaded holes 208 are distally located with respect to the lateral centerline 224 and threaded holes 210 are proximally located with respect to the lateral centerline 224 (shown). In this embodiment, for central hole pairs 226a and 226b, which fall on either side of lateral centerline 224, threaded holes 210a and 210b may be in close proximity to one another on either side of the lateral centerline 224 (shown). In another embodiment, threaded holes 210 may be distally located with respect to the lateral centerline 224 and non-threaded holes 208 may be proximally located with respect to the lateral centerline 224 (not shown). In this embodiment, for central hole pairs that fall on either side of lateral centerline 224, non-threaded holes 208 may be in close proximity to one another on either side of the lateral centerline 224 (not shown).

As should be appreciated, bone plate 200 is exemplary and explanatory and is intended to provide further explanation of the claims. However, it is contemplated that bone plate 200 may have more or fewer features within the spirit of the present disclosure and description of the various features of bone plate 200 is not intended to be limiting.

Figure 3A:
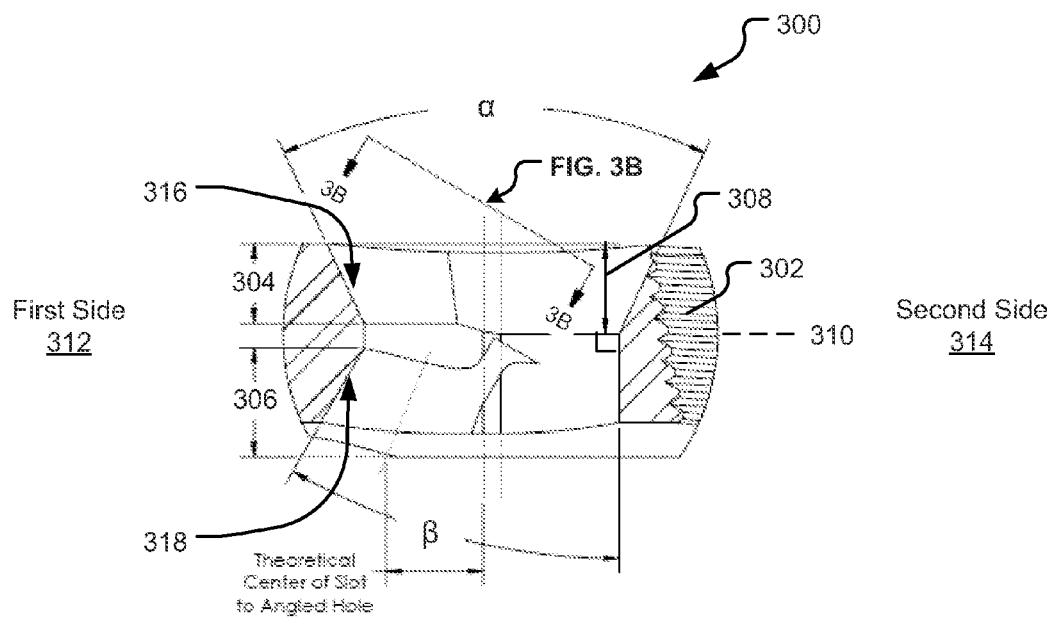
FIGS. 3A-3B are diagrams illustrating multiple views of an embodiment of a non-threaded hole.
Figure 3B:
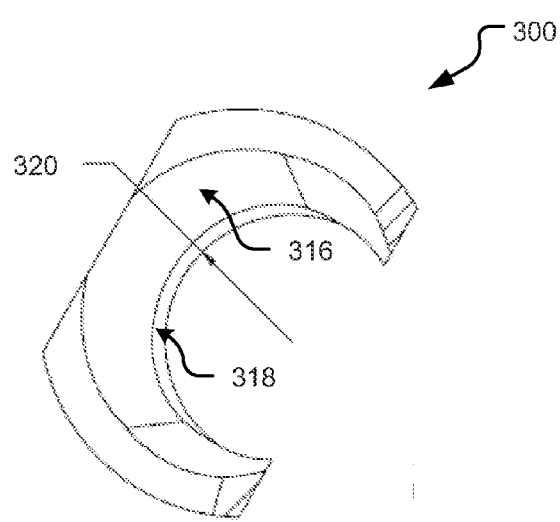

FIGS. 3A and 3B are diagrams illustrating multiple views of an embodiment of a non-threaded hole.

FIG. 3A is a diagram illustrating a cross-sectional view of an embodiment of a non-threaded hole 300. Non-threaded hole 300 is substantially similar to non-threaded hole 208 as illustrated in FIG. 2A.

As described above, a non-threaded hole may have an internal geometry that is different from an internal geometry of a threaded hole. For example, a non-threaded hole is adapted to receive a compression screw. Additionally, as described above, a non-threaded hole may be part of a hole pair. In embodiments, the internal geometry of non-threaded hole 300 may be asymmetrical and may be based at least in part on a spatial orientation of the non-threaded hole 300 with respect to an adjacent threaded hole 302 in a hole pair. As described above, in embodiments, the spatial orientation of non-threaded and threaded holes within hole pairs on one side of a lateral centerline of the bone plate (e.g., lateral centerline 224) is a mirror image of the spatial orientation of non-threaded and threaded holes within hole pairs on the other side of the lateral centerline.

For example, an interior geometry of non-threaded hole 300 may be defined by a first side 312 that is distal from threaded hole 302 and a second side 314 that is proximal to threaded hole 302. In embodiments, non-threaded hole 300 may comprise an upper tapered region 316 that is substantially conical and defined by an angle α. The upper tapered region 316 may extend to a first depth 304 on the first side 312 of the non-threaded hole and to a second depth 308 on the second side 314 of the non-threaded hole. In some embodiments, second depth 308 may be greater than first depth 304. In further embodiments, second depth 308 may extend to approximately a horizontal centerline 310 of the bone plate.

As illustrated by FIG. 3A, non-threaded hole 300 may also comprise a lower tapered region 318. On the first side 312 of the non-threaded hole, the lower tapered region 318 may be substantially conical and defined by an angle β. The lower tapered region 318 may extend a third depth 306 from the bottom surface of the bone plate. On the second side 314 of the non-threaded hole, the lower tapered region 318 may not be tapered and may be defined by a substantially right angle with respect to horizontal centerline 310. Thus, while the lower tapered region 318 is tapered on first side 312, it is not substantially tapered on second side 314.

In embodiments, while the above description of non-threaded hole 300 is described with respect to a first and second side, it is to be appreciated that non-threaded hole 300 is three-dimensional, as illustrated by FIG. 3B.

FIG. 3B is a diagram illustrating a top perspective view of an embodiment of a non-threaded hole 300. FIG. 3B is viewed from a perspective "3B" that is identified in FIG. 3A. FIG. 3B illustrates a top perspective view of upper tapered region 316 and lower tapered region 318.

Radius 320 is the radius of the angled cut whose axis is at angle beta. In embodiments, radius 320 is sufficient to allow a minor diameter of a compression screw to pass through non-threaded hole 300.

As described above, bone reduction may be accomplished using compression screws. As will be described further below, a compression screw has a threaded shaft and an enlarged head having an upper surface and a lower surface. In general, a compression screw passes through a non-threaded hole, through the bone plate, and into two or more bone fragments. As the compression screw engages deeper within the bone, the lower surface of the enlarged head is brought into contact with the upper tapered region of the non-threaded hole (e.g., upper tapered region 316), thereby drawing the bone plate toward the bone. Thus, upon tightening the compression screw, the two or more bone fragments are pulled together under a compression load against the bottom surface of the bone plate.

In addition, bones may fracture in any number of various ways and it is often necessary to draw bone fragments together at different angles. Thus, in embodiments, the internal geometry of non-threaded hole 300 enables a compression screw to be inserted at any of a plurality of different angles. For example, in one embodiment, with reference to FIG. 3A, a compression screw may be inserted such that a shaft portion of the compression screw is angled toward threaded hole 302 and such that an enlarged head portion of the compression screw is angled away from threaded hole 302. Further, in this embodiment, a lower surface of an enlarged head of the compression screw contacts the first side 312 of the upper tapered region 316 of non-threaded hole 300.

In another embodiment, with reference to FIG. 3A, a compression screw may be inserted such that the shaft portion of the compression screw is angled away from threaded hole 302 and such that the enlarged head portion of the compression screw is angled toward threaded hole 302. Further, in this embodiment, the lower surface of the enlarged head of the compression screw contacts the second side 314 of the upper tapered region 316 of non-threaded hole 300. Indeed, as the non-threaded holes of the present disclosure are substantially cylindrical with conical tapering, the enlarged head portion of the compression screw may contact the upper tapered region 316 at various angles and orientations around substantially the full circumference of the non-threaded hole.

As described above, some prior bone plate systems were provided with "combination holes." These combination holes involved a single hole with a threaded portion and a non-threaded portion. Accordingly, as only a portion of the combination hole is non-threaded, only a portion of the combination hole is suitable for placement of a compression screw. That is, a compression screw should be placed in the combination hole such that the enlarged head of the compression screw contacts the non-threaded portion of the combination hole (i.e., the enlarged head should be angled toward the non-threaded portion of the combination hole). Indeed, if a compression screw it placed such that the enlarged head of the compression screw is seated against the threaded portion of the combination hole, the compression screw will exhibit an unacceptably high profile above the bone plate. In contrast, present embodiments allow the compression screw to be inserted at virtually any angle because the upper tapered region is provided around the full perimeter of the non-threaded hole.

As should be appreciated, non-threaded hole 300 is exemplary and explanatory and is intended to provide further explanation of the claims. However, it is contemplated that non-threaded hole 300 may have more or fewer features within the spirit of the present disclosure and description of the various features of non-threaded hole 300 is not intended to be limiting.

Figure 4:
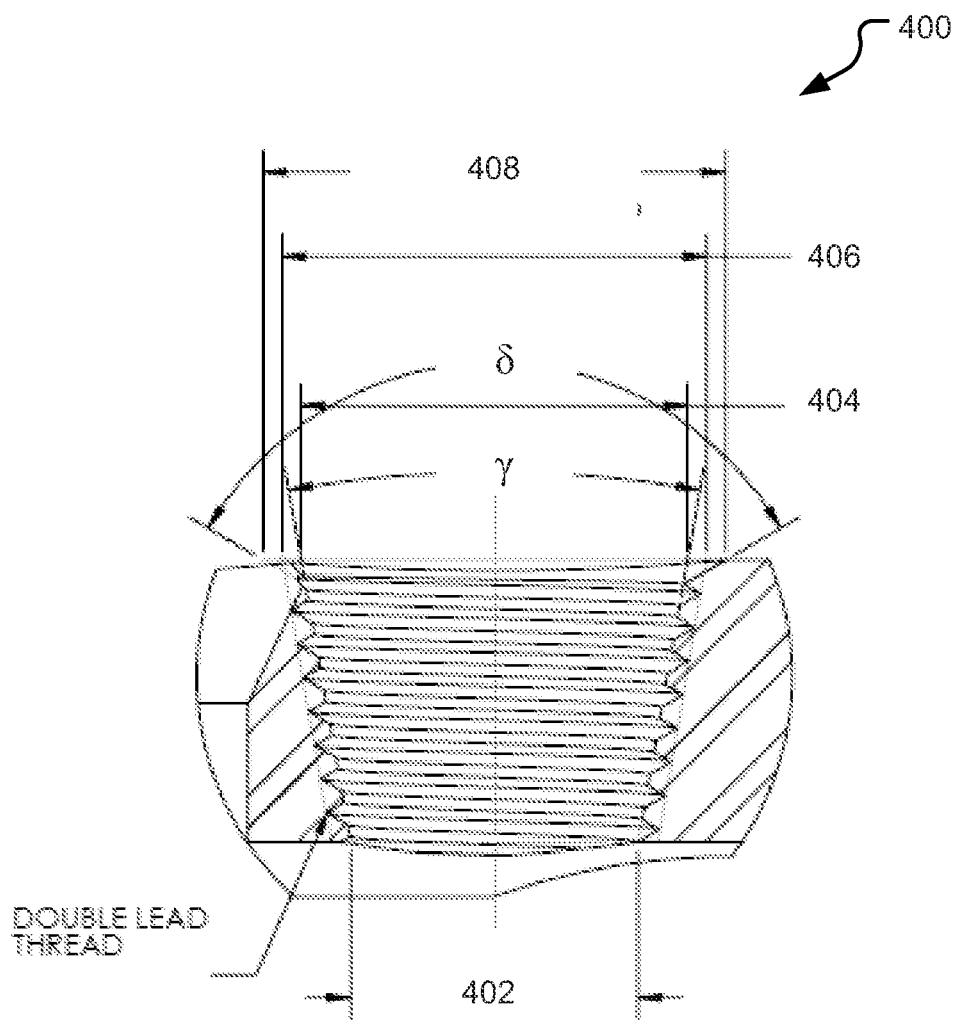
FIG. 4 is a diagram illustrating a cross-sectional view of an embodiment of a threaded hole.

FIG. 4 is a diagram illustrating a cross-sectional view of an embodiment of a threaded hole 400. Threaded hole 400 is substantially similar to threaded hole 210 as illustrated in FIG. 2A.

As described above, a threaded hole may have an internal geometry that is different from an internal geometry of a non-threaded hole. For example, a threaded hole may be adapted to engage threads on a head of a locking screw. In contrast to a combination hole, which is only partially threaded, threaded hole 400 is threaded around its full circumference. Accordingly, threaded hole 400 is adapted to engage threads around the full circumference of the head of a locking screw. It should be appreciated that full engagement of a threaded head of a locking screw provides greater stability between the locking screw and the bone plate than partial engagement of the threaded head of a locking screw.

As described above, a threaded hole may be part of a hole pair. In embodiments, the internal geometry of a threaded hole 400 may be substantially symmetrical. For example, the internal geometry of threaded hole 400 may be tapered from a top surface through the bone plate to a bottom surface. The taper of threaded hole 400 may be defined by an angle $\gamma$. In some embodiments, threads of threaded hole 400 may have a dual lead such that a first lead is offset about 180 degrees from a second lead, requiring minimal rotation of the locking screw to engage the threaded hole 400.

Threaded hole 400 may further be defined by a minor thru-diameter 402 at the bottom surface of the bone plate. The minor thru-diameter 402 is a minimum diameter required such that a particular sized locking screw is able to pass through the bone plate and into the bone. The threads of threaded hole 400 may further be defined by a minor diameter 404 and a major diameter 406.

In embodiments, threaded hole 400 may also comprise a chamfer or beveled edge at the top surface of the bone plate. The chamfer may be provided to smooth a transition from the threaded internal geometry of threaded hole 400 to the top surface of the bone plate, e.g., to reduce or prevent smooth tissue irritation. The chamfer also serves to aide insertion of the screw into the threaded hole. In embodiments, the chamfer may have a chamfer diameter 408 defined by an angle $\delta$. In some embodiments, angle $\delta$ may be about 120 degrees. In embodiments, the chamfer diameter 408 may be greater than the minor diameter 404 and the major diameter 406.

As should be appreciated, threaded hole 400 is exemplary and explanatory and is intended to provide further explanation of the claims. However, it is contemplated that threaded hole 400 may have more or fewer features within the spirit of the present disclosure and description of the various features of threaded hole 400 is not intended to be limiting.

Figure 5:
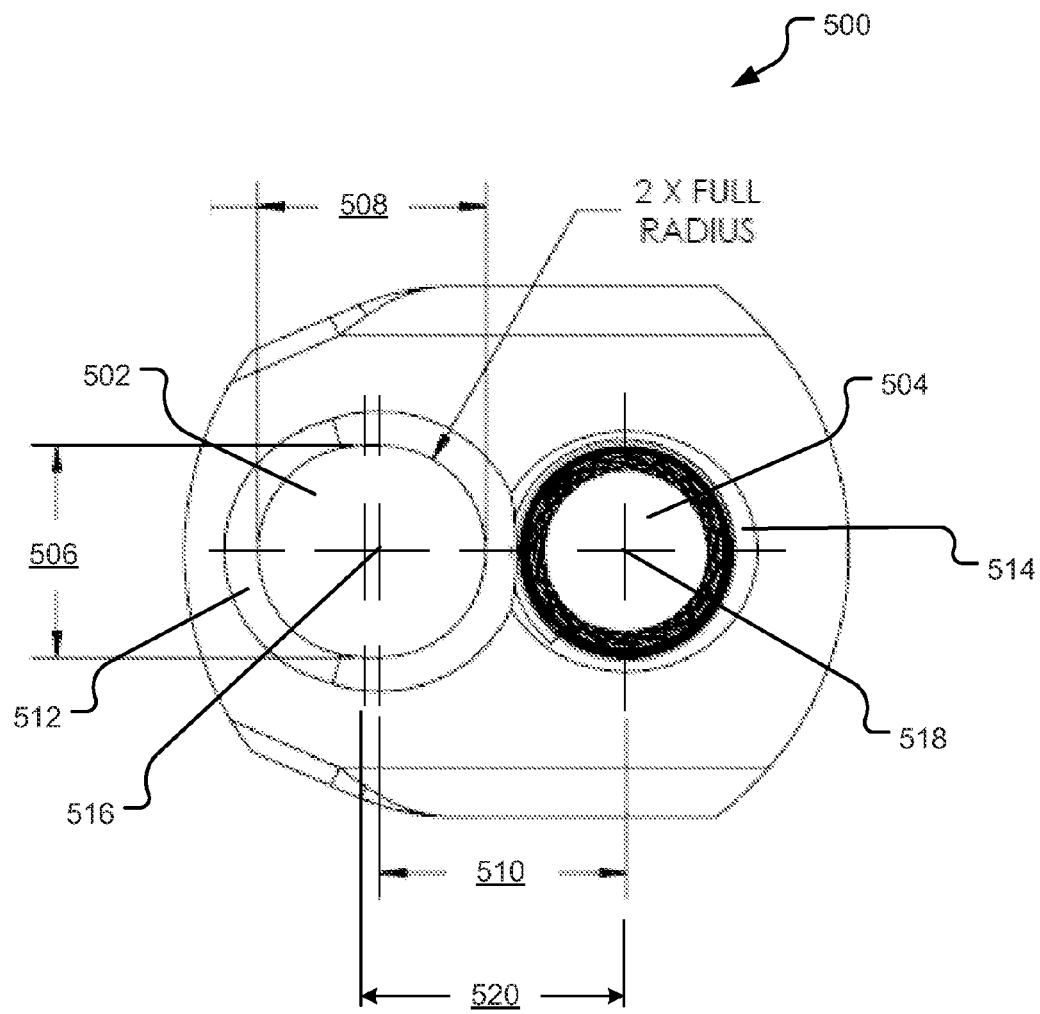
FIG. 5 is a diagram illustrating a top view of an embodiment of a hole pair.

FIG. 5 is a diagram illustrating a top view of an embodiment of a hole pair 500.

As illustrated by FIG. 5, a non-threaded hole 502 and a threaded hole 504 are provided in close proximity to form the hole pair 500. In embodiments, the non-threaded hole 502 and the threaded hole 504 remain distinct holes within hole pair 500, but are close enough so as to maximize the number of holes on the bone plate and to facilitate the insertion of either or both of a compression screw and a locking screw in close proximity. For example, in embodiments, non-threaded hole 502 and threaded hole 504 may be closely arranged such that at least a portion of the non-threaded hole 502 overlaps the threaded hole 504. In embodiments, an upper tapered region 512 of non-threaded hole 502 may overlap a chamfer 514 of threaded hole 504. In other embodiments, a chamfer (not shown) of non-threaded hole 502 may overlap a chamfer 514 of threaded hole 504. In further embodiments, non-threaded hole 502 and threaded hole 504 may be closely arranged such that a first center point 516 of non-threaded hole 502 may be located at a distance 510 from a second center point 518 of threaded hole 504.

In embodiments, at least a portion of the non-threaded hole 502 overlaps the threaded hole 504 in hole pair 500. Thus, in embodiments, distance 510 is less than a distance from first center point 516 to second center point 518 when the non-threaded hole 502 and threaded hole 504 are placed side-by-side. Thus, embodiments maximize a number of hole pairs provided in a bone plate by minimizing a distance between the non-threaded hole and the threaded hole of each hole pair.

In additional embodiments, non-threaded hole 502 is at least partially elongated along a longitudinal diameter and threaded hole 504 is substantially circular (or cylindrical). For example, non-threaded hole 502 may have a longitudinal diameter 508 that is greater than a lateral diameter 506. For example, in some cases, the longitudinal diameter may be about 5 mm and the lateral diameter may be about 4.5 mm.

As described above, non-threaded holes may be particularly adapted for compression screws and threaded holes may be particularly adapted for locking screws. For example, in embodiments, an upper tapered region and a lower tapered region of a non-threaded hole may enable insertion of compression screws at different angles. In contrast, a threaded hole comprises threads adapted to mate with threads on a head of a locking screw, which serve to secure the locking screw to the bone plate at a substantially fixed angular orientation. Accordingly, while it is possible to insert a compression screw in a threaded hole, the threaded hole does not allow the compression screw to be inserted at different angles, greatly decreasing a surgeon's ability to properly reduce a bone fracture. Additionally, a threaded hole does not comprise an upper tapered region. Thus, if a compression screw is inserted in a threaded hole, the enlarged head of the compression screw has a higher profile above the top surface of the bone plate than when a compression screw is seated down in the upper tapered region of a non-threaded hole. As soft tissue irritation may be caused by rough, irregular or protruding surfaces on a bone plate, it is preferable for a compression screw to have a lower profile above the top surface of a bone plate. Moreover, a non-threaded hole is poorly adapted for a locking screw because the purpose of a locking screw is to secure the locking screw to the bone plate, which requires engaging the threads of the locking screw with the threads of a threaded hole.

It should be appreciated that threaded and non-threaded holes perform distinct roles with respect to properly reducing a bone fracture using a bone plate. Thus, embodiments herein seek to retain the distinct features of a threaded hole and a non-threaded hole while increasing the overall number and combination of threaded and non-threaded holes on a bone plate. Additionally, embodiments herein seek to provide full contact of a screw head around the circumference of either type of hole. This approach provides marked advantages over a combination hole, which involves a threaded portion and a non-threaded portion within a single hole. For instance, as described above, the threaded portion of a combination hole does not fully engage the threads around the circumference of the head of a locking screw, reducing stability between the locking screw and the bone plate. Moreover, the non-threaded portion of a combination hole limits the angles at which a compression screw may be inserted. Additionally, in contrast to the present embodiments, which allow a locking screw and a compression screw to be inserted in close proximity, a surgeon is forced to choose between inserting a compression screw or a locking screw in any particular combination hole.

As should be appreciated, hole pair 500 is exemplary and explanatory and is intended to provide further explanation of the claims. However, it is contemplated that hole pair 500 may have more or fewer features within the spirit of the present disclosure and description of the various features of hole pair 500 is not intended to be limiting.

Figure 6:
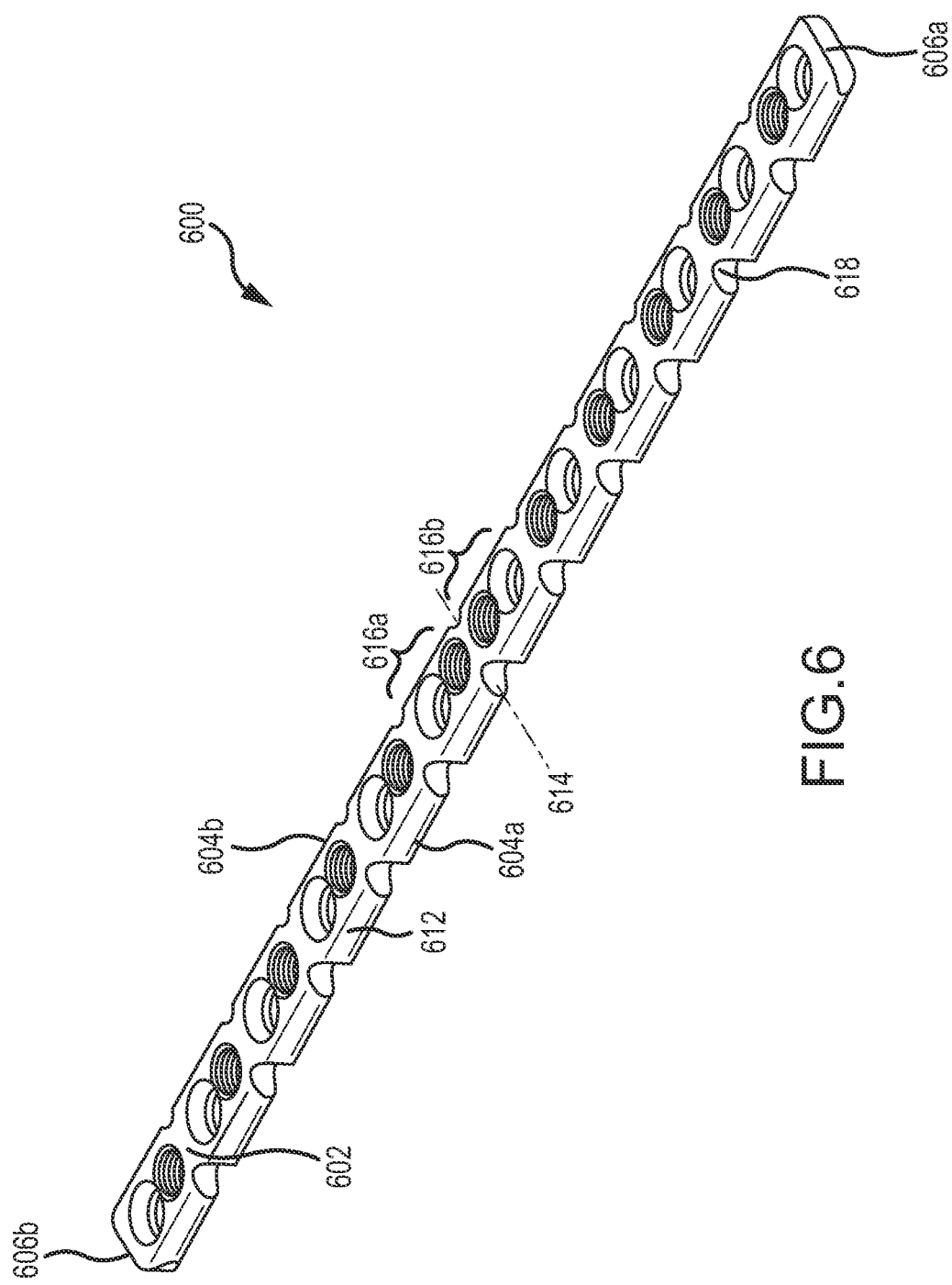
FIG. 6 is a diagram illustrating a perspective view of an embodiment of a bone plate.

FIG. 6 is a diagram illustrating a perspective view of an embodiment of a bone plate 600.

Bone plate 600 has a top surface 602 that is relatively smooth and a smooth, rounded transition 612 from top surface 602 to lateral surface 604. Unlike bone plate 100, bone plate 600 comprises relatively blunt plate ends 606a and 606b. As bone plate 600 does not comprise tapered plate ends, bone plate 600 may be suited for more-invasive surgical procedures.

Bone plate 600 further comprises one or more non-threaded holes 608 and one or more threaded holes 610. In embodiments, a non-threaded hole 608 is configured to receive a compression screw and a threaded hole 610 is configured with threads to engage a threaded head of a locking screw. In embodiments, the bone plate 600 is further provided with one or more hole pairs (e.g., hole pairs 616a and 616b) in which a non-threaded hole 608 and a threaded hole 610 are placed adjacent to one another.

Bone plate 600 is further illustrated with a lateral centerline 614. Similar to bone plate 200, features of bone plate 600 are mirrored at lateral centerline 614. For example, in one embodiment, each hole pair may be arranged such that non-threaded holes 608 are distally located with respect to the lateral centerline 614 and threaded holes 610 are proximally located with respect to the lateral centerline 614 (shown). In this embodiment, central hole pairs 616a and 616b are mirror images such that the threaded holes 610 are adjacent to one another on either side of lateral centerline 614 (shown). In another embodiment, threaded holes 610 may be distally located with respect to the lateral centerline 614 and non-threaded holes 608 may be proximally located with respect to the lateral centerline 614 (not shown).

As illustrated in FIG. 6, bone plate 600 may also comprise one or more indentations 618 along lateral sides 604a and 604b. In embodiments, indentations 618 are provided to facilitate bending bone plate 600 to conform to a particular bone.

As should be appreciated, bone plate 600 is exemplary and explanatory and is intended to provide further explanation of the claims. However, it is contemplated that bone plate 600 may have more or fewer features within the spirit of the present disclosure and description of the various features of bone plate 600 is not intended to be limiting.

Figure 7:
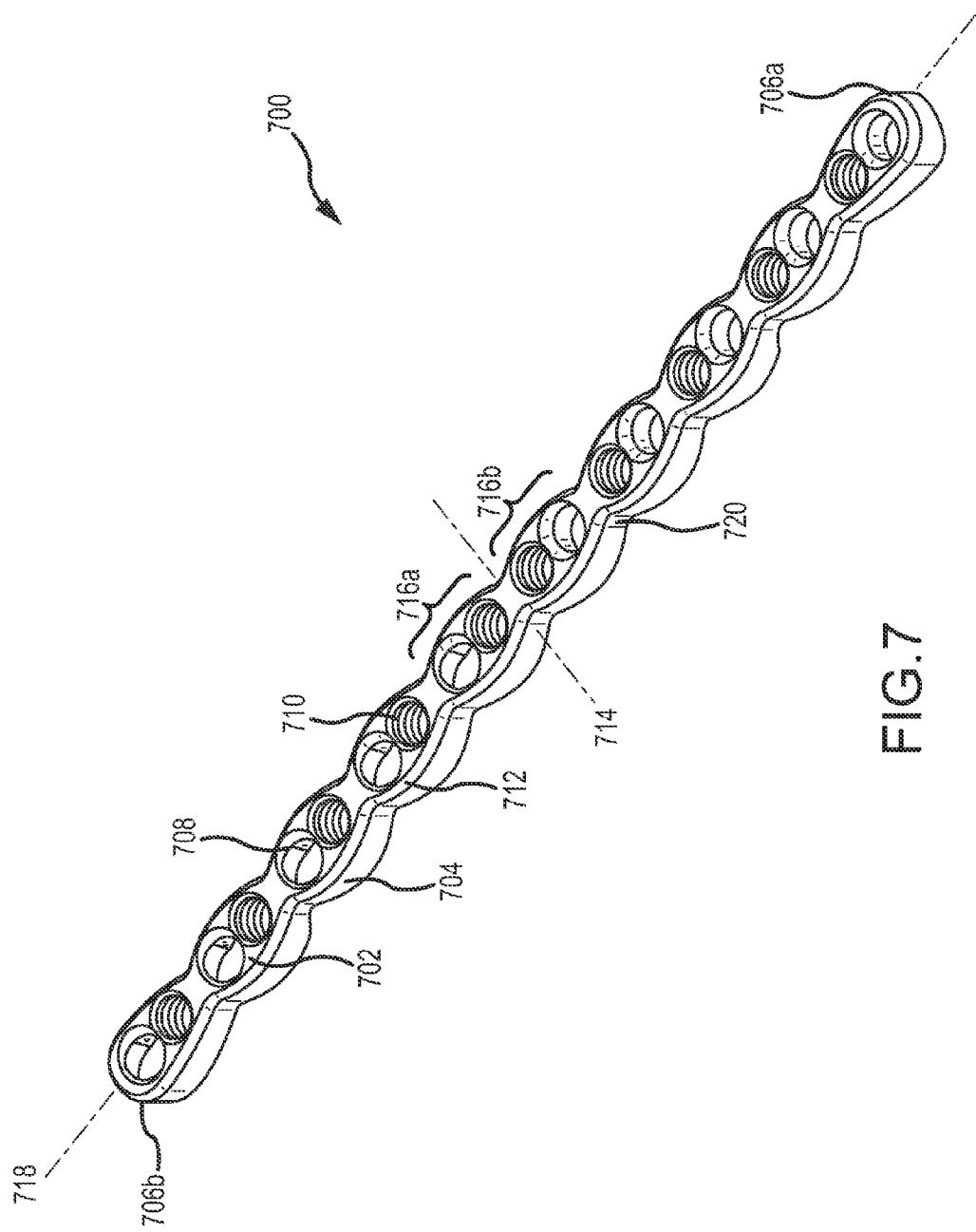
FIG. 7 is a diagram illustrating a perspective view of an embodiment of a bone plate.

FIG. 7 is a diagram illustrating a perspective view of an embodiment of a bone plate 700.

Bone plate 700 has a top surface 702 that is relatively smooth and a tapered transition 712 from top surface 702 to lateral surface 704. Bone plate 700 also comprises rounded plate ends 706a and 706b.

Bone plate 700 further comprises one or more non-threaded holes 708 and one or more threaded holes 710. In embodiments, a non-threaded hole 708 is configured to receive a compression screw and a threaded hole 710 is configured with threads to engage a threaded head of a locking screw. In embodiments, the bone plate 700 is further provided with one or more hole pairs (e.g., hole pairs 716a and 716b) in which a non-threaded hole 708 and a threaded hole 710 are placed adjacent to one another.

Bone plate 700 is further illustrated with a lateral centerline 714. Similar to bone plate 200, features of bone plate 700 are mirrored at lateral centerline 714. For example, in one embodiment, each hole pair may be arranged such that non-threaded holes 708 are distally located with respect to the lateral centerline 714 and threaded holes 710 are proximally located with respect to the lateral centerline 714 (shown). In this embodiment, central hole pairs 716a and 716b are mirror images such that the threaded holes 710 are adjacent to one another on either side of lateral centerline 714 (shown). In another embodiment, threaded holes 710 may be distally located with respect to the lateral centerline 714 and non-threaded holes 708 may be proximally located with respect to the lateral centerline 714 (not shown).

Bone plate 700 may also comprise one or more tapered regions 720 where bone plate 700 narrows toward longitudinal centerline 718. In embodiments, a tapered region 720 may be provided between each hole pair (e.g., hole pairs 716a and 716b). In further embodiments, tapered regions 720 are provided to facilitate bending bone plate 700 to conform to a particular bone.

As should be appreciated, bone plate 700 is exemplary and explanatory and is intended to provide further explanation of the claims. However, it is contemplated that bone plate 700 may have more or fewer features within the spirit of the present disclosure and description of the various features of bone plate 700 is not intended to be limiting.

Figure 8:
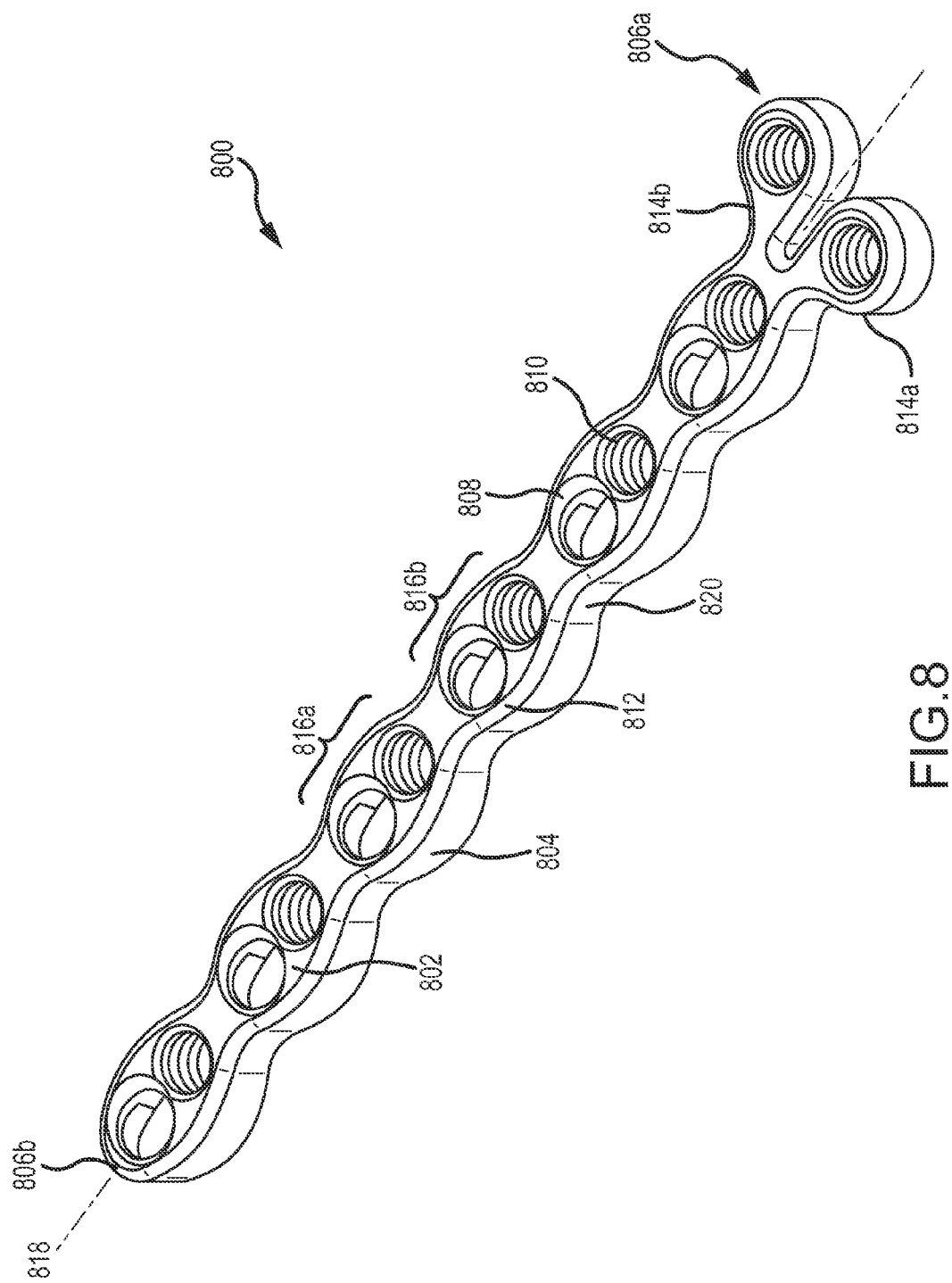
FIG. 8 is a diagram illustrating a perspective view of an embodiment of a bone plate.

FIG. 8 is a diagram illustrating a perspective view of an embodiment of a bone plate 800.

In embodiments, bone plate 800 is a condylar plate. Condylar plates generally have a head portion (as opposed to a straight plate) and a shaft portion. The headed portion and the shaft portion generally have holes, including threaded, non-threaded, or both types of holes. The head portion is configured to fit on the condyle of a bone (i.e., the rounded end of a bone) and the shaft portion is configured to fit along the longitudinal axis of the bone. Moreover, a condylar plate may be contoured during surgery to fit to the bone around the condyle and then screws are inserted through one or both head holes into the condyle portion of the bone. Screws may also be inserted along the shaft portion of the bone plate and into the longitudinal section of the bone.

Bone plate 800 has a top surface 802 that is relatively smooth and a tapered transition 812 from top surface 802 to lateral surface 804. Bone plate 800 also comprises a shaft portion between an expanded plate end 806a and a rounded plate end 806b. Unlike rounded plate end 806b, expanded plate end 806a may comprise two or more lateral extensions, e.g., lateral extensions 814a and 814b. In embodiments, expanded plate end 806a may not comprise a hole pair. In some embodiments, expanded plate end 806a may comprise one or more threaded holes 810, e.g., a threaded hole 810 in each lateral extension 814a and 814b (shown). In other embodiments, expanded plate end 806a may comprise one or more non-threaded holes 808, e.g., a non-threaded hole 808 in each lateral extension 814a and 814b (not shown). In still other embodiments, expanded plate end 806a may comprise at least one threaded hole 810 and at least one non-threaded hole 808, e.g., e.g., a non-threaded hole 808 in one lateral extension and a threaded hole 810 in another lateral extension (not shown).

The shaft portion of bone plate 800 further comprises one or more non-threaded holes 808 and one or more threaded holes 810. In embodiments, a non-threaded hole 808 is configured to receive a compression screw and a threaded hole 810 is configured with threads to engage a threaded head of a locking screw. In embodiments, the bone plate 800 is further provided with one or more hole pairs (e.g., hole pairs 816a and 816b) in which a non-threaded hole 808 and a threaded hole 810 are placed adjacent to one another.

Bone plate 800 may also comprise one or more tapered regions 820 where bone plate 800 narrows toward longitudinal centerline 818. In embodiments, a tapered region 820 may be provided between each hole pair (e.g., hole pairs 816a and 816b). In further embodiments, tapered regions 820 are provided to facilitate bending bone plate 800 to conform to a particular bone.

As should be appreciated, bone plate 800 is exemplary and explanatory and is intended to provide further explanation of the claims. However, it is contemplated that bone plate 800 may have more or fewer features within the spirit of the present disclosure and description of the various features of bone plate 800 is not intended to be limiting.

FIGS. 9A and 9B are diagrams illustrating multiple views of an embodiment of a locking screw.

FIG. 9A illustrates a lateral view of an embodiment of a locking screw 900.

As described above, threads on a head of a locking screw are adapted to engage or mate with threads in a threaded hole in order to stabilize a bone plate. In embodiments, the locking screw is adapted to be secured in a bone plate at a substantially fixed angular orientation.

For example, as illustrated by FIG. 9A, locking screw 900 may have a total length 902. Total length 902 may be any suitable length, e.g., from about 10 mm to about 60 mm. In embodiments, locking screw 900 includes a head 904 and a shaft 906. In embodiments, the head 904 further comprises head threads 910. Head threads 910 may be adapted to engage threads in a threaded hole of a bone plate. Shaft 906 comprises shaft threads 908 that are adapted to engage bone and a flute 912 adapted for self-tapping into bone. Locking screw 900 may further comprise a centerline 914.

In embodiments, locking screw 900 may be adapted to engage both with a bone plate and with bone to provide a fixed angular relationship between the bone plate and the locking screw 900, reducing the incidence of loosening or movement of the bone plate in relation to the bone.

FIG. 9B illustrates a cross-sectional view of an embodiment of a locking screw 900.

As illustrated by FIG. 9B, locking screw 900 has a head that is tapered by an angle γ'. The tapered head of locking screw 900 is adapted to fit within a threaded hole that is tapered by a corresponding angle γ. Additionally, the tapered head may comprise a recess 920 adapted to accept a drill bit for rotating and inserting the locking screw 900 into a threaded hole. In embodiments, locking screw 900 further comprises a minor diameter 916 and a major diameter 918 (identified in circle "C" of screw 900).

As should be appreciated, locking screw 900 is exemplary and explanatory and is intended to provide further explanation of the claims. However, it is contemplated that locking screw 900 may have more or fewer features within the spirit of the present disclosure and description of the various features of locking screw 900 is not intended to be limiting.

FIGS. 10A and 10B are diagrams illustrating multiple views of an embodiment of a compression screw.

FIG. 10A illustrates a lateral view of an embodiment of a compression screw 1000.

As described above, a compression screw is adapted to engage bone to reduce a bone fracture by pulling bone fragments together. In embodiments, the compression screw is adapted to be inserted through a bone plate and into underlying bone at a variety of angles.

For example, as illustrated by FIG. 10A, compression screw 1000 may have a total length 1010. Total length 1010 may be any suitable length, e.g., from about 10 mm to about 110 mm. In embodiments, compression screw 1000 includes an enlarged head 1012 having an upper surface 1004 and a lower surface 1006. Compression screw 1000 may further comprise a shaft 1014 with threads 1002 that are adapted to engage bone and a flute 1016 adapted for self-tapping into bone. In embodiments, compression screw 1000 also comprises a neck 1008 between enlarged head 1012 and shaft 1014. As described above, to reduce a bone fracture, the lower surface 1006 of the enlarged head 1012 may be brought into contact with an upper tapered region of a non-threaded hole as threads 1002 engage two or more bone fragments to draw them together under a compression load against a bottom surface of a bone plate.

FIG. 10B illustrates a cross-sectional view of an embodiment of a compression screw 1000.

As illustrated by FIG. 10B, compression screw 1000 has an enlarged head 1012 having a head diameter 1018 and defined by a distance 1020 from the upper surface 1004 to the lower surface 1006 of the enlarged head (identified in circle "B" of screw 1000). Additionally, the enlarged head 1012 may comprise a recess 1026 adapted to accept a drill bit for rotating and inserting the compression screw 1000 through a non-threaded hole and into bone. Shaft 1014 of compression screw 1000 may be further defined by a minor diameter 1022 and a major diameter 1024 (identified in circle "C" of screw 1000).

As should be appreciated, compression screw 1000 is exemplary and explanatory and is intended to provide further explanation of the claims. However, it is contemplated that compression screw 1000 may have more or fewer features within the spirit of the present disclosure and description of the various features of compression screw 1000 is not intended to be limiting.

Figure 11:
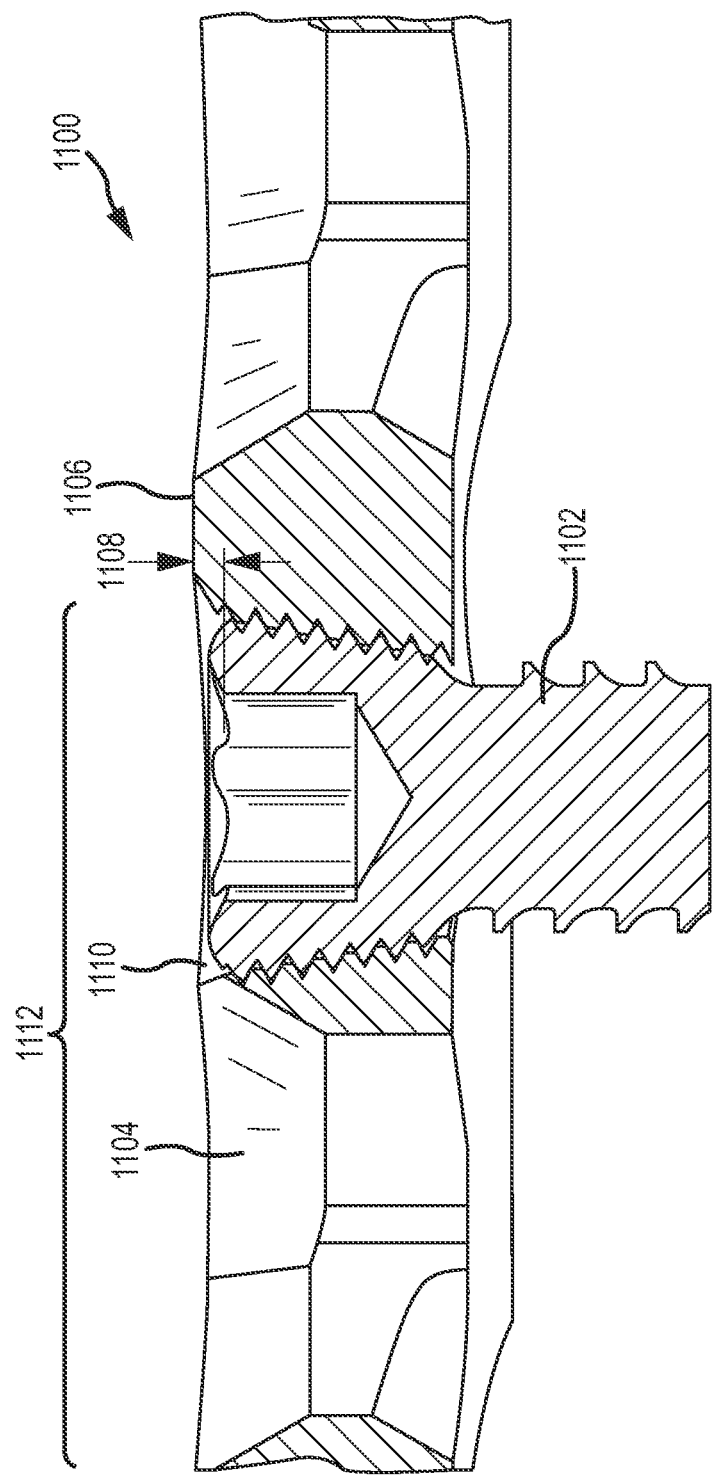
FIG. 11 is a diagram illustrating an embodiment of a locking screw inserted in a threaded hole.

FIG. 11 is a diagram illustrating an embodiment of a locking screw inserted in a threaded hole.

As illustrated by FIG. 11, a locking screw 1102 is inserted in a threaded hole 1110 adjacent to a non-threaded hole 1104 in a hole pair 1112 of bone plate 1100. In embodiments, locking screw 1102 is recessed below top surface 1106 of bone plate 1100 by a distance 1108. Distance 1108 ranges from about 0.0 mm (flush with top surface) to about 0.4 mm below top surface 1106 (shown). In some embodiments, distance 1108 is greater than a distance that a typical locking screw is recessed in a bone plate, e.g., about 0.3 mm greater. As described above, a thickness of bone plate 1100 may be optimized to increase the structural integrity of the bone plate while at the same time maximizing the number of holes in the bone plate. Additionally, increasing the thickness of the bone plate 1100 enables locking screw 1102 to exhibit a lower profile with respect to top surface 1106. It will be appreciated that the lower profile of locking screw 1102 reduces the likelihood of soft tissue irritation caused by bone plate 1100.

As should be appreciated, bone plate 1100 and locking screw 1102 are exemplary and explanatory and are intended to provide further explanation of the claims. However, it is contemplated that bone plate 1100 and locking screw 1102 may have more or fewer features within the spirit of the present disclosure and description of the various features of bone plate 1100 and locking screw 1102 is not intended to be limiting.

Figure 12:
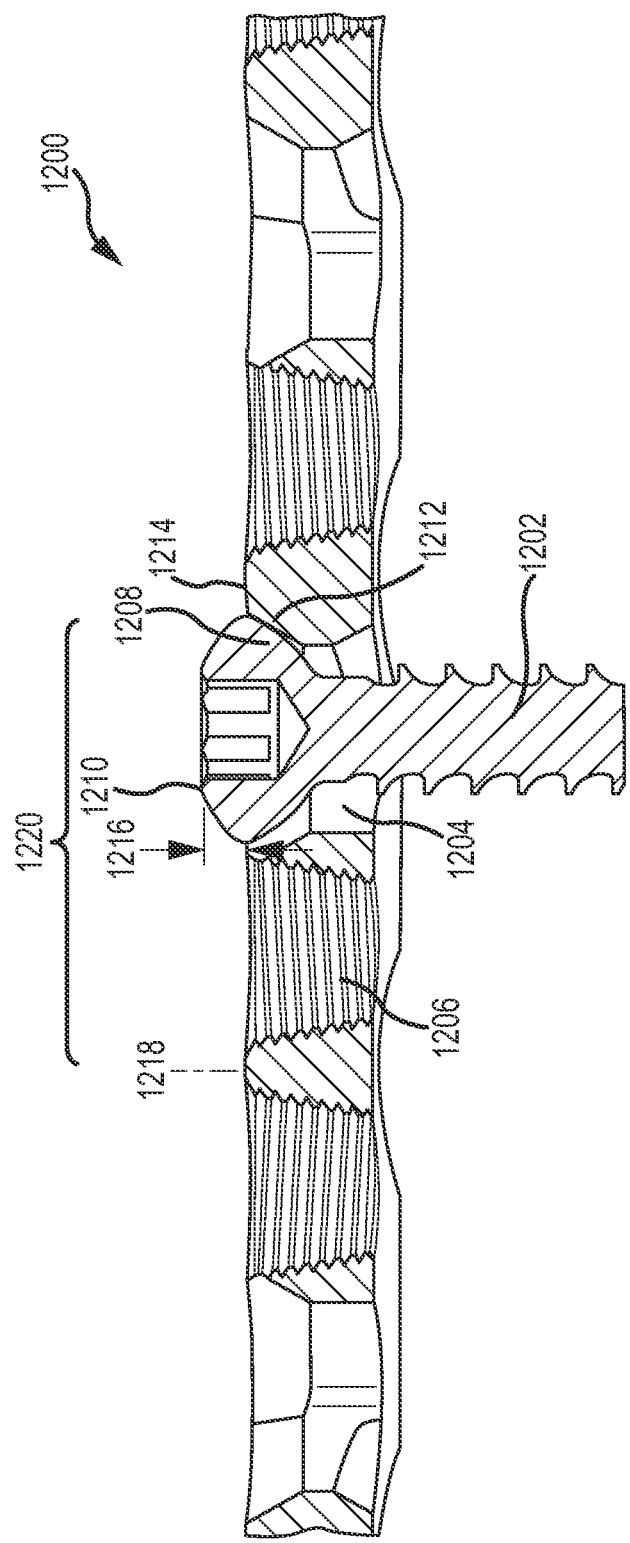
FIG. 12 is a diagram illustrating an embodiment of a compression screw inserted in a non-threaded hole.

FIG. 12 is a diagram illustrating an embodiment of a compression screw inserted in a non-threaded hole.

As illustrated by FIG. 12, a compression screw 1202 is inserted in a non-threaded hole 1204 adjacent to a threaded hole 1206 in a hole pair 1220 of bone plate 1200. As illustrated, a lower surface 1208 of an enlarged head 1210 of compression screw 1202 is in contact with an upper tapered region 1212 of non-threaded hole 1204. In the illustrated embodiment, compression screw 1202 is in contact with a distal side of the upper tapered region 1212 with respect to centerline 1218.

In embodiments, the enlarged head 1210 of compression screw 1202 protrudes above top surface 1214 by a profile 1216. Profile 1216 may range from about 0.5 mm to about 1.2 mm. In embodiments, profile 1216 is lower than a typical profile for a compression screw seated in a bone plate, e.g., about 0.3 mm lower than a typical profile. As described above, a thickness of bone plate 1200 may be optimized to increase the structural integrity of the bone plate while at the same time maximizing the number of holes in the bone plate. In embodiments, increasing the thickness of bone plate 1200 enables compression screw 1202 to be seated lower in non-threaded hole 1204, resulting in a lower profile with respect to top surface 1214. It will be appreciated that the lower profile of compression screw 1202 reduces the likelihood of soft tissue irritation caused by bone plate 1200.

As should be appreciated, bone plate 1200 and compression screw 1202 are exemplary and explanatory and are intended to provide further explanation of the claims. However, it is contemplated that bone plate 1200 and compression screw 1202 may have more or fewer features within the spirit of the present disclosure and description of the various features of bone plate 1200 and compression screw 1202 is not intended to be limiting.

Figure 13:
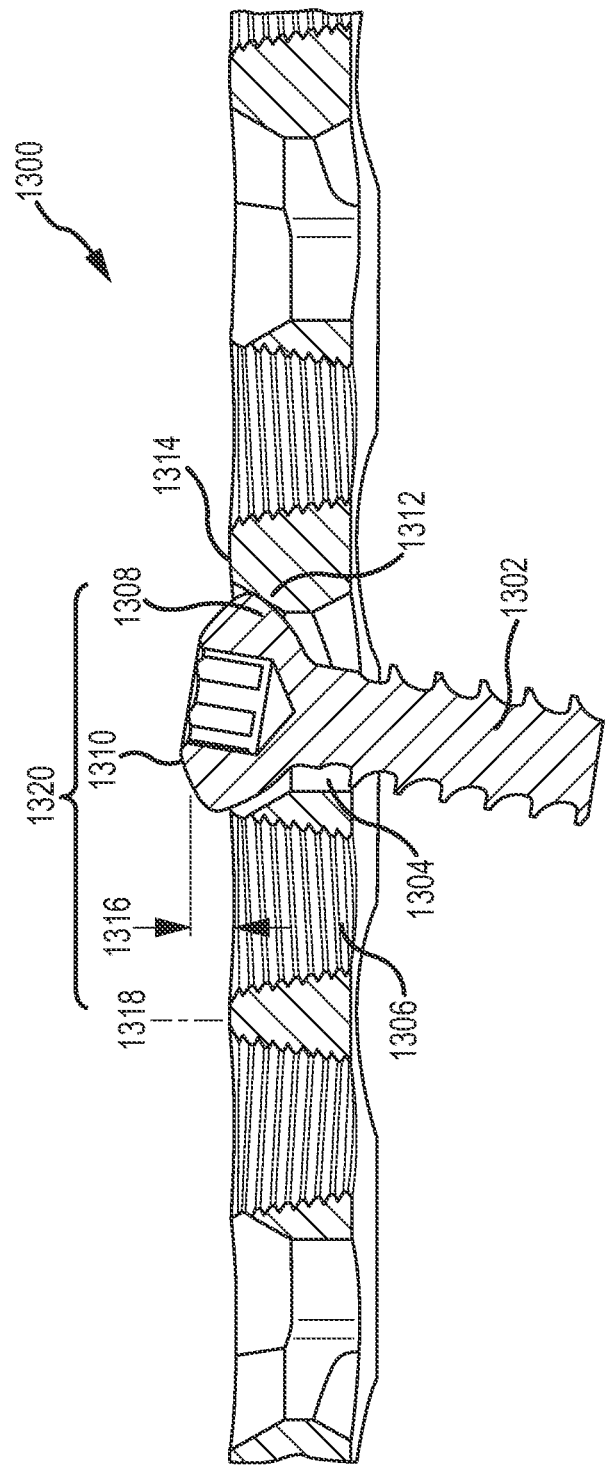
FIG. 13 is a diagram illustrating an embodiment of a compression screw inserted in a non-threaded hole at an angle.

FIG. 13 is a diagram illustrating an embodiment of a compression screw inserted in a non-threaded hole at an angle toward a centerline of a bone plate.

As illustrated by FIG. 13, a compression screw 1302 is inserted in a non-threaded hole 1304 adjacent to a threaded hole 1306 in a hole pair 1320 of bone plate 1300. As illustrated, a lower surface 1308 of an enlarged head 1310 of compression screw 1302 is in contact with an upper tapered region 1312 of non-threaded hole 1304.

As described above, bones may fracture in any number of various ways and it is often necessary to draw bone fragments together at different angles. Thus, as illustrated by FIG. 13, the internal geometry of non-threaded hole 1304 enables compression screw 1302 to be inserted at an angle. In the illustrated embodiment, compression screw 1302 is in contact with a distal side of the upper tapered region 1312 such that a shaft of compression screw 1302 is angled toward threaded hole 1306 and centerline 1318 of the bone plate 1300.

In the illustrated embodiment, the enlarged head 1310 of compression screw 1302 protrudes above top surface 1314 by a profile 1316 when it is inserted at an angle toward the centerline 1318. Profile 1316 may range from about 0.75 mm to about 1.5 mm. In embodiments, profile 1316 is lower than a typical profile for a compression screw seated at an angle toward the center of a bone plate, e.g., about 0.3 mm lower than a typical profile. In embodiments, increasing the thickness of bone plate 1300 enables compression screw 1302 to be seated lower in non-threaded hole 1304, resulting in a lower profile with respect to top surface 1314. It will be appreciated that the lower profile of compression screw 1302 reduces the likelihood of soft tissue irritation caused by bone plate 1300.

As should be appreciated, bone plate 1300 and compression screw 1302 are exemplary and explanatory and are intended to provide further explanation of the claims. However, it is contemplated that bone plate 1300 and compression screw 1302 may have more or fewer features within the spirit of the present disclosure and description of the various features of bone plate 1300 and compression screw 1302 is not intended to be limiting.

Figure 14:
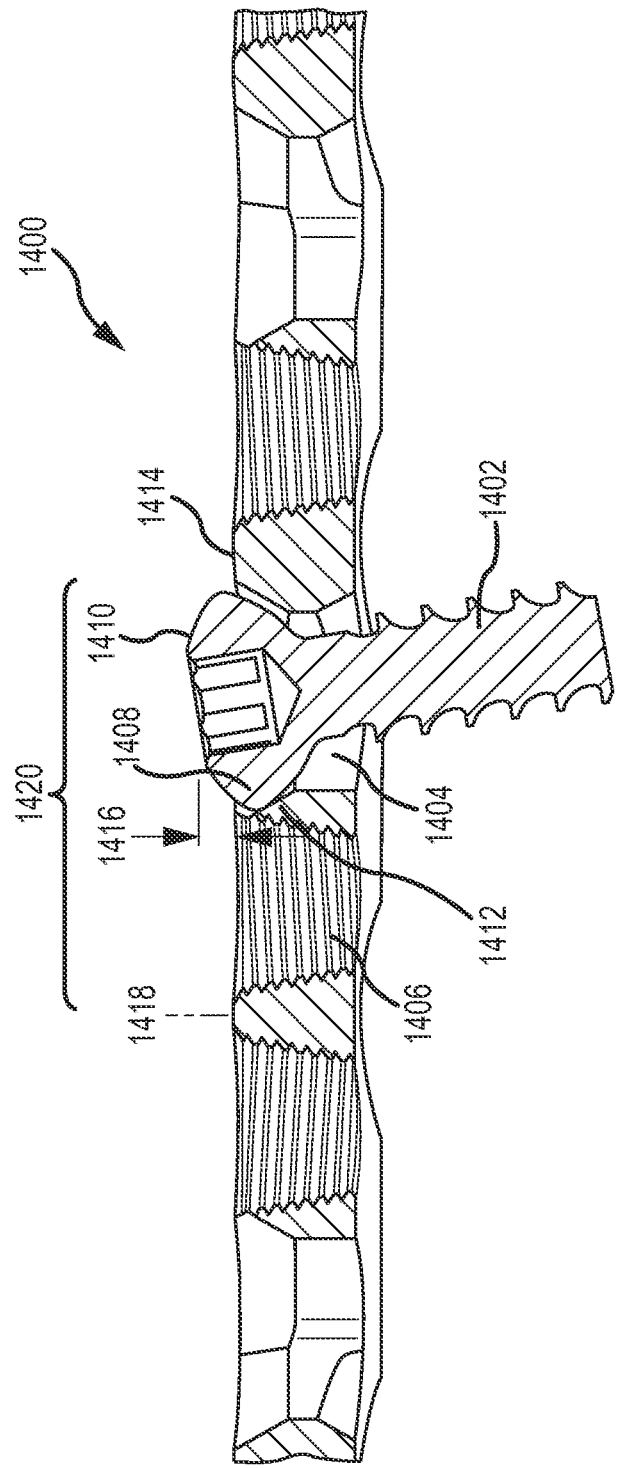
FIG. 14 is a diagram illustrating an embodiment of a compression screw inserted in a non-threaded hole at an angle.

FIG. 14 is a diagram illustrating an embodiment of a compression screw inserted in a non-threaded hole at an angle away from a centerline of a bone plate.

As illustrated by FIG. 14, a compression screw 1402 is inserted in a non-threaded hole 1404 adjacent to a threaded hole 1406 in a hole pair 1420 of bone plate 1400. As illustrated, a lower surface 1408 of an enlarged head 1410 of compression screw 1402 is in contact with an upper tapered region 1412 of non-threaded hole 1404. In the illustrated embodiment, the internal geometry of non-threaded hole 1404 enables compression screw 1402 to be inserted at an angle. For example, compression screw 1402 is in contact with a proximal side of the upper tapered region 1412 such that a shaft of compression screw 1402 is angled away from threaded hole 1406 and centerline 1418 of the bone plate 1400.

In the illustrated embodiment, the enlarged head 1410 of compression screw 1402 protrudes above top surface 1414 by a profile 1416 when it is inserted at an angle away from the centerline 1418. Profile 1416 may range from about 1.2 mm to about 2.0 mm. In embodiments, profile 1416 is lower than a typical profile for a compression screw seated at an angle away from the center of a bone plate, e.g., about 0.3 mm less than a typical profile. In embodiments, increasing the thickness of bone plate 1400 enables compression screw 1402 to be seated lower in non-threaded hole 1404, resulting in a lower profile with respect to top surface 1414. It will be appreciated that the lower profile of compression screw 1402 reduces the likelihood of soft tissue irritation caused by bone plate 1400.

As should be appreciated, bone plate 1400 and compression screw 1402 are exemplary and explanatory and are intended to provide further explanation of the claims. However, it is contemplated that bone plate 1400 and compression screw 1402 may have more or fewer features within the spirit of the present disclosure and description of the various features of bone plate 1400 and compression screw 1402 is not intended to be limiting.

Figure 15:
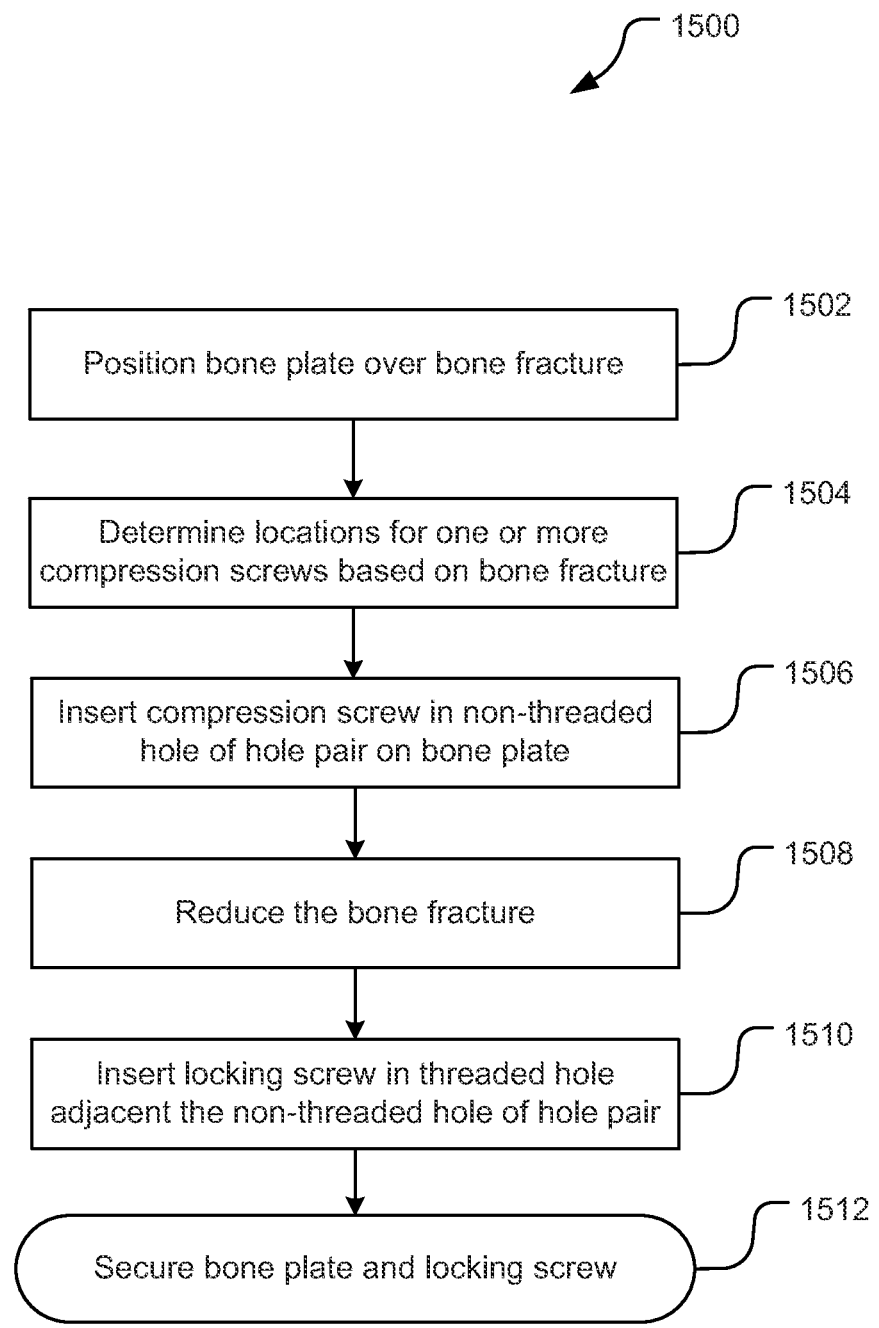
FIG. 15 is a flow chart illustrating an embodiment of a method for reducing a bone fracture.

FIG. 15 is a flow chart illustrating an embodiment of a method for reducing a bone fracture.

As should be appreciated, the particular steps of method 1500 described above are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present disclosure.

At operation 1502, a bone plate is positioned over a bone fracture. As described above, bone plates are generally constructed of metal, e.g., titanium, and may be fabricated in a number of different shapes and sizes to conform to different types of bone for use with different types of fractures. At operation 1502, the bone plate is placed over the bone fracture such that the bone fragments may be properly drawn together to reduce the bone fracture.

At operation 1504, locations for one or more compression screws are determined based on aligning the bone fracture with available non-threaded holes on the bone plate. In embodiments, a bone plate that has a plurality of hole pairs provides additional options for aligning and placing the one or more compression screws. For example, as a locking screw, a compression screw, or both, may be placed in each hole pair, a total number of screws and different screw combinations that may be inserted in the bone plate is increased.

At operation 1506, a compression screw is inserted in a non-threaded hole of a hole pair on a bone plate. In general, a compression screw passes through a non-threaded hole, through the bone plate, and into two or more bone fragments. Upon tightening the compression screw, the two or more bone fragments are pulled together under a compression load against the bottom surface of the bone plate. As described above, a non-threaded hole may have an internal geometry that is adapted to receive a compression screw. For example, the internal geometry of a non-threaded hole enables a compression screw to be inserted at any of a plurality of different angles to properly draw the bone fragments together.

At operation 1508, a bone fracture is reduced by bringing bone fragments into alignment and close proximity to facilitate the body's natural bone growth and healing. In embodiments, as the compression screw engages deeper within the bone, the lower surface of an enlarged head of the compression screw is brought into contact with an upper tapered region of the non-threaded hole, thereby drawing the bone plate toward the bone. Thus, upon tightening the compression screw, two or more bone fragments of the bone fracture are pulled together under a compression load against the bottom surface of the bone plate to reduce the bone fracture.

At operation 1510, a locking screw is inserted in a threaded hole adjacent to the non-threaded hole of the hole pair. As described above, seating of a locking screw in a threaded hole secures the threaded head of the locking screw to the bone plate to maintain a fixed angular relationship between the locking screw and the bone plate. In embodiments, a non-threaded hole and a threaded hole may be provided in close proximity in a hole pair. In this case, the non-threaded hole and the threaded hole remain distinct holes within the hole pair, but are close enough to maximize the number of holes on the bone plate and to facilitate the insertion of either or both of a compression screw and a locking screw in close proximity, which facilitates both reduction of the bone and stabilization of the bone plate.

At operation 1512, a bone plate is secured in a fixed angular relationship to the locking screw. Accordingly, as the locking screw engages both the bone plate and the bone in the fixed angular relationship, the incidence of loosening or movement of the bone plate in relation to the bone is minimized. In embodiments, reduction of the bone and securing of the bone plate is facilitated using a bone plate having a plurality of hole pairs. In embodiments, hole pairs maximize a total number of screws and different combinations of screws that may be inserted in the bone plate.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A bone plate for reducing a bone fracture, comprising:
   a top surface and a bottom surface;
   a threaded hole passing through the top surface, through a substantially solid interior region and out the bottom surface of the bone plate, threads of the threaded hole extending from the top surface, wherein the threaded hole engages a threaded head of a locking screw to stabilize the bone plate; and
   a non-threaded hole passing through the top surface, through the substantially solid interior region and out the bottom surface of the bone plate, wherein the non-threaded hole receives a compression screw to reduce the bone fracture, wherein at least a portion of the threaded hole overlaps at least a portion of the non-threaded hole, and wherein the threaded hole and the non-threaded hole are distinct holes.

2. The bone plate of claim 1, wherein a chamfer of the non-threaded hole at least partially overlaps a chamfer of the threaded hole.

3. The bone plate of claim 1, wherein a hole pair is formed by the threaded hole and the non-threaded hole.

4. The bone plate of claim 3, wherein the number of hole pairs is maximized along a longitudinal axis of the bone plate.

5. The bone plate of claim 4, wherein the bottom surface of the bone plate includes scallops adjusted to maximize the number of hole pairs along the longitudinal axis of the bone plate.

6. The bone plate of claim 1, wherein a screw seated in one of the non-threaded hole or the threaded hole has a reduced profile.

7. The bone plate of claim 1, wherein the bone plate concurrently accepts the locking screw in the threaded hole and the compression screw in the non-threaded hole.

8. The bone plate of claim 1, wherein an internal geometry of the non-threaded hole accepts the compression screw at a plurality of different angles.

9. The bone plate of claim 1, wherein the threads of the threaded hole extend from the top surface to the bottom surface of the bone plate.

10. The bone plate of claim 1, wherein the non-threaded hole has a longitudinal diameter that is greater than a lateral diameter.

11. The bone plate of claim 1, wherein the non-threaded hole is non-cylindrical.

12. A bone plate for reducing a bone fracture, comprising:
    a top surface and a bottom surface; and
    at least one hole pair including:
        a threaded hole passing through the top surface, through a substantially solid interior region and out the bottom surface of the bone plate, threads of the threaded hole extending from the top surface, wherein the threaded hole accepts a first screw; and
        a non-threaded hole passing through the top surface, through the substantially solid interior region and out the bottom surface of the bone plate, wherein the non-threaded hole accepts a second screw, wherein the threaded hole and the non-threaded hole are distinct holes in close proximity to one another.

13. The bone plate of claim 12, wherein at least a portion of the threaded hole overlaps at least a portion of the non-threaded hole.

14. The bone plate of claim 12, wherein the number of hole pairs is maximized along a longitudinal axis of the bone plate.

15. The bone plate of claim 14, wherein the bottom surface of the bone plate includes scallops adjusted to maximize the number of hole pairs along the longitudinal axis of the bone plate.

16. The bone plate of claim 12, wherein a screw seated in one of the non-threaded hole or the threaded hole has a reduced profile.

17. The bone plate of claim 12, wherein the bone plate concurrently accepts the first screw in the threaded hole and the second screw in the non-threaded hole.

18. The bone plate of claim 12, wherein an internal geometry of the non-threaded hole accepts the second screw at a plurality of different angles.

19. The bone plate of claim 12, wherein the threads of the threaded hole extend from the top surface to the bottom surface of the bone plate.

20. The bone plate of claim 12, wherein the non-threaded hole has a longitudinal diameter that is greater than a lateral diameter.

21. The bone plate of claim 12, wherein the non-threaded hole is non-cylindrical.

\* \* \* \* \*